(12) United States Patent
Lee et al.

(10) Patent No.: US 9,417,204 B2
(45) Date of Patent: Aug. 16, 2016

(54) ANALYTE SENSOR

(75) Inventors: Eric Lee, Sunnyvale, CA (US); Mark Micklatcher, Sunnyvale, CA (US); Jai Krishnamurthy, Sunnyval, CA (US)

(73) Assignee: Senova Systems, Inc., Sunnyvale, CA (US)

( * ) Notice: Subject to any disclaimer, the term of this patent is extended or adjusted under 35 U.S.C. 154(b) by 318 days.

(21) Appl. No.: 13/812,135

(22) PCT Filed: Jul. 26, 2011

(86) PCT No.: PCT/US2011/045385
§ 371 (c)(1),
(2), (4) Date: Mar. 19, 2013

(87) PCT Pub. No.: WO2012/018632
PCT Pub. Date: Feb. 9, 2012

(65) Prior Publication Data
US 2013/0168609 A1    Jul. 4, 2013

Related U.S. Application Data

(60) Provisional application No. 61/367,590, filed on Jul. 26, 2010.

(51) Int. Cl.
*G01N 27/30* (2006.01)
*C07F 7/08* (2006.01)

(52) U.S. Cl.
CPC ............... *G01N 27/30* (2013.01); *C07F 7/081* (2013.01); *G01N 27/302* (2013.01); *C08L 2312/08* (2013.01)

(58) Field of Classification Search
None
See application file for complete search history.

(56) References Cited

U.S. PATENT DOCUMENTS

| | | | |
|---|---|---|---|
| 4,906,103 A | 3/1990 | Kao | |
| 5,223,117 A * | 6/1993 | Wrighton et al. | 204/415 |
| 5,496,521 A | 3/1996 | Leiner | |
| 5,507,936 A | 4/1996 | Hatschek et al. | |
| 6,004,442 A * | 12/1999 | Choulga et al. | 204/416 |
| 6,353,323 B1 | 3/2002 | Fuggle | |
| 6,395,158 B1 | 5/2002 | King et al. | |
| 6,987,184 B2 | 1/2006 | Sakata et al. | |
| 7,132,403 B2 | 11/2006 | Cichewicz et al. | |
| 2003/0111344 A1 | 6/2003 | Yamaoka | |
| 2003/0180964 A1* | 9/2003 | Yang et al. | 436/166 |

(Continued)

FOREIGN PATENT DOCUMENTS

| | | |
|---|---|---|
| GB | 2451596 A * | 2/2009 |
| JP | 11119458 A * | 4/1999 |

(Continued)

OTHER PUBLICATIONS

English text translation of Nukada et al. (JP 11119458 A) accessed on the AIPN JPO website and attached to the case file as two PDFs (part 1 and part 2).*

(Continued)

*Primary Examiner* — Harold Pyon
*Assistant Examiner* — Katie L Hammer
(74) *Attorney, Agent, or Firm* — David R. Conklin; Kirton McConkie

(57) ABSTRACT

Matrix materials, such as sol-gels and polymers derivatives to contain a redox active material can be used to form electrodes and probes suitable for use in pH meters and other analyte sensing devices.

15 Claims, 2 Drawing Sheets

(56) References Cited

U.S. PATENT DOCUMENTS

| | | |
|---|---|---|
| 2005/0093556 A1 | 5/2005 | Mueller et al. |
| 2005/0183494 A1 | 8/2005 | Tess et al. |
| 2006/0003457 A1 | 1/2006 | Porter et al. |
| 2008/0023328 A1* | 1/2008 | Jiang et al. .................. 204/407 |
| 2008/0035481 A1 | 2/2008 | McCormack et al. |
| 2008/0182136 A1 | 7/2008 | Arnold et al. |
| 2008/0302660 A1 | 12/2008 | Kahn et al. |

FOREIGN PATENT DOCUMENTS

| | | |
|---|---|---|
| JP | 2004-229617 A | 8/2004 |
| JP | 2006-223218 A | 8/2006 |
| WO | 2005085825 A1 | 9/2005 |
| WO | 2007/034131 A1 | 3/2007 |
| WO | 2007/106936 A1 | 9/2007 |

OTHER PUBLICATIONS

Akhoury, Abhinav et al., "Redox-Responsive Gels with Tunable Hydrophobicity for Controlled Solubilization and Release of Organics," ACS Appl. Mater. Interfaces, pp. 1167-1174, 2011.

Richter, Andreas et al., "Review on Hydrogel-based pH Sensors and Microsensors," Sensors, pp. 561-581, 2008.

Cantau, C. et al., "Oxidation of Nauseous Sulfur Compounds by Photocatalysis or Photosensitization," Catalysis Today, vol. 122, Issues 1-2, Apr. 15, 2007, pp. 8-19.

Jusoh, Norhana et al., "Immobilization of Glucose Oxidase and Ferrocene Redox Polymer in Cross-Linked Poly (Vinyl Alcohol) with Bovine Serum Albumin as Protein Stabilizer," Regional Postgraduate Conference On Engineering and Science (RPCES) 2006, 2006.

Arkles, Barry, "Gelest Silane Coupling Agents: Connecting Across Boundaries," Gelest, Inc., pp. 1-60, 2006.

* cited by examiner

ANALYTE SENSOR

This application is a National Stage of International Application No. PCT/US2011/045385, filed Jul. 26, 2011, and entitled ANALYTE SENSOR, which claims the benefit of U.S. Provisional Application No. 61/367,590, filed Jul. 26, 2010. This application claims priority to and incorporates herein by reference the above-referenced application in its entirety.

BACKGROUND OF THE INVENTION

The present invention relates generally to technology for detecting an analyte. In various embodiments, the invention relates to devices for measuring pH, the potential of hydrogen, which is a measure of the acidity or alkalinity of a solution. The pH of a solution is determined by the concentration of dissolved hydrogen ions ($H^+$) (also referred to as hydronium ions, $H_3O^+$) within the solution. As the concentration of dissolved hydrogen ions within the solution increases, the solution becomes more acidic. Conversely, the solution becomes more basic as the concentration of dissolved hydrogen ions within the solution decreases. The concentration of dissolved hydrogen ions within a solution has traditionally been measured with a glass electrode connected to an electronic meter that displays the pH reading. Traditionally the terms "probe" and "electrode" have been used interchangeably to describe a functional grouping of component electrodes. As used herein, the term "electrode" is used to refer to a specific electrode in a probe, i.e., such as a "working electrode", a "reference electrode", or a "counter electrode", and "probe" refers to a functional grouping of electrodes sufficient to generate a signal that can be processed to generate a reading indicative of the concentration of an analyte of interest in a solution.

The traditional glass pH probe has a working electrode (WE) that is an ion-selective electrode made of a fragile, doped glass membrane sensitive to hydrogen ions. The pH-responsive glass membrane is the primary analyte sensing element in this type of probe and so is referred to as the "working" electrode. Hydrogen ions within the sample solution bind to the outside of the glass membrane, thereby causing a change in potential on the interior surface of the membrane. This change in potential is measured against the constant potential of a conventional reference electrode (RE), such as an electrode based on silver/silver chloride. The difference in potential is then correlated to a pH value by plotting the difference on a calibration curve. The calibration curve is created through a tedious, multistep process whereby the user plots changes in potential for various known buffer standards. Traditional pH meters are based on this principle.

The response of traditional glass working electrodes (and probes and meters containing them) to pH is unstable, and glass probes periodically require careful calibration involving tedious, time-consuming processes, multiple reagents, and a well trained operator. The special properties and construction of the glass probes further require that the glass membrane be kept wet at all times. Thus, routine care of the glass probe requires regular performance of cumbersome and costly storage, rinsing, cleaning, and calibration protocols performed by a well trained operator to ensure proper maintenance and working performance.

In addition to tedious maintenance and storage requirements, traditional glass probes are fragile, thereby limiting the fields of application of the glass probe. In particular, the fragile nature of the glass probe makes it unsuitable for use in food and beverage applications, as well as use in unattended, harsh, or hazardous environments. Accordingly, there is a need in the art for pH probes and meters (as well as other analyte probes and meters) that address and overcome the limitations of traditional pH probes and meters employing the glass probe.

In response to the limitations described above for traditional glass probe pH measuring systems, voltammetric systems were proposed to offer a more robust system for the determination of pH. In a voltammetric system, an electrical potential is applied in a controlled manner, typically varied linearly with time, and the corresponding current flowing through a conductive material is monitored by means of, for example, a potentiostat (see, for example, Wang, "Analytical Electrochemistry," $3^{rd}$ ed, John Wiley & Sons, 2006). Initial proposals (see U.S. Pat. No. 5,223,117) were based on the concept of a WE composed of a conductive substrate with a redox active molecule attached to its surface. The hypothesis was that, provided an appropriate "analyte-sensitive", redox active material (ASM) was used, the potential at which the maximum current flows in this system would be a function of the pH of the analyte solution. However, this initial proposal met with little enthusiasm, perhaps because it was demonstrated with an electrode that used gold as a substrate.

Significant advances were made in both theory and research laboratory practice of voltammetry-based analyte sensing systems when researchers discovered that carbon could replace gold as the conductive substrate and, moreover, that, regardless of the substrate, mixtures of redox active materials could be used in voltammetric systems (see PCT Pub. Nos. 2005/066618 and 2005/085825). One particularly intriguing proposal by these researchers was that a mixture of "analyte-sensitive" materials (ASMs) and "analyte-insensitive" materials (AIMs) could be attached to a conductive substrate and effectively convert it into both a WE (signal generated by the ASM) and a reference electrode (RE) (signal generated by the AIM). No significant advances, however, in either theory or practice were made for some time after these initial proposals and research (see, e.g., PCT Pub. Nos. 2007/034131 and 2008/154409).

The next significant advance in the field occurred when scientists discovered that, in practice, no redox active material is completely "analyte-insensitive" and that practical application of voltammetric technology should focus on WEs without AIMs. These scientists also discovered, however, that, regardless of whether a redox active material was characterized as an ASM or AIM, it could be made truly analyte-insensitive by sequestration in an ionic medium. This discovery led to the analyte-insensitive electrode or AIE, which could not only be used as a replacement of the conventional RE in traditional pH measuring systems but could also be used with WEs based on voltammetry. See PCT Pub. No. 2010/104962. Soon after these discoveries, pH meters suitable for use on the laboratory benchtop and for important research and development applications were created. See PCT Pub. Nos. 2010/111531 and 2010/118156.

However, despite these highly promising advances, in practice, the useful lifetime of, and suitable applications for, these probes were dependent, among other factors, on the means by which the redox active molecules were affixed to the substrate surface of the electrode. For example, the two main approaches for attaching the redox active molecule to the substrate of the electrode, non-covalent adsorption and direct chemical (covalent) linkage, both exhibit rapidly decaying signals, some losing much of their functionality in less than two days, and instability in certain analyte solutions or environmental conditions.

There is, therefore, a need in the art for methods and compositions for fixing redox active materials to the conductive substrate of an electrode for use in a voltammetry-based analyte-sensing system and for electrodes, probes, pH meters, and other analyte sensing devices based on voltammetric systems that provide longer useful lifetimes and can be used for a wider variety of applications. The present invention meets these needs.

SUMMARY OF THE INVENTION

The present invention relates generally to methods for immobilizing a redox active material to a conductive substrate, compounds, and compositions useful in the method, electrodes produced by the method, and pH meters and other analyte sensing devices incorporating one or more electrodes of the invention.

In one aspect, the invention relates to methods for immobilizing redox active compounds in matrix materials that can be coated on the surface of a suitable substrate or molded to form a redox active surface for use in analyte-sensing electrodes, probes, and sensors, such as pH meters and other analyte-sensing devices. The method is generally applicable to any redox active compound, but in many embodiments, is practiced using the AIMs or ASMs known to be useful in voltammetry-based analyte-sensing methodology. In the method, the AIM or ASM is covalently attached to the polymer that forms the matrix. In some embodiments, the AIM or ASM is first attached to a monomer unit that is then polymerized to form the matrix material. In other embodiments, the AIM or ASM is attached to a polymer that may be used directly or cross-linked and then used. Variations and combinations of these embodiments are also provided.

In another aspect, the invention relates to electrode components, electrodes, probes, and meters comprising one or more matrix materials of the invention. In one embodiment, the invention provides a working electrode that contains a matrix material of the invention comprising an ASM coated on an electrically conductive substrate such that it remains in electrical contact with the substrate. The present invention also provides sensors such as pH meters and other analyte sensing devices comprising such WEs. In some embodiments, the matrix material in these WEs can also have one or more AIMs attached to them. In another embodiment, the invention provides an AIE that contains a matrix material of the invention comprising either an ASM or AIM or both. In any of these embodiments, the matrix material of the invention can be coated onto the surface of a distinct electrically conductive substrate to form an electrode (or component thereof) or can be molded to form the electrode (or component).

In another aspect, the present invention relates to compounds, compositions, and methods for the formation of the matrix materials of the invention. In one embodiment, the invention provides compounds, compositions and methods for forming sol-gel matrix materials. In another embodiment, the invention provides compounds, compositions and methods for forming other polymeric matrix materials.

DETAILED DESCRIPTION OF THE INVENTION

Figure 1:
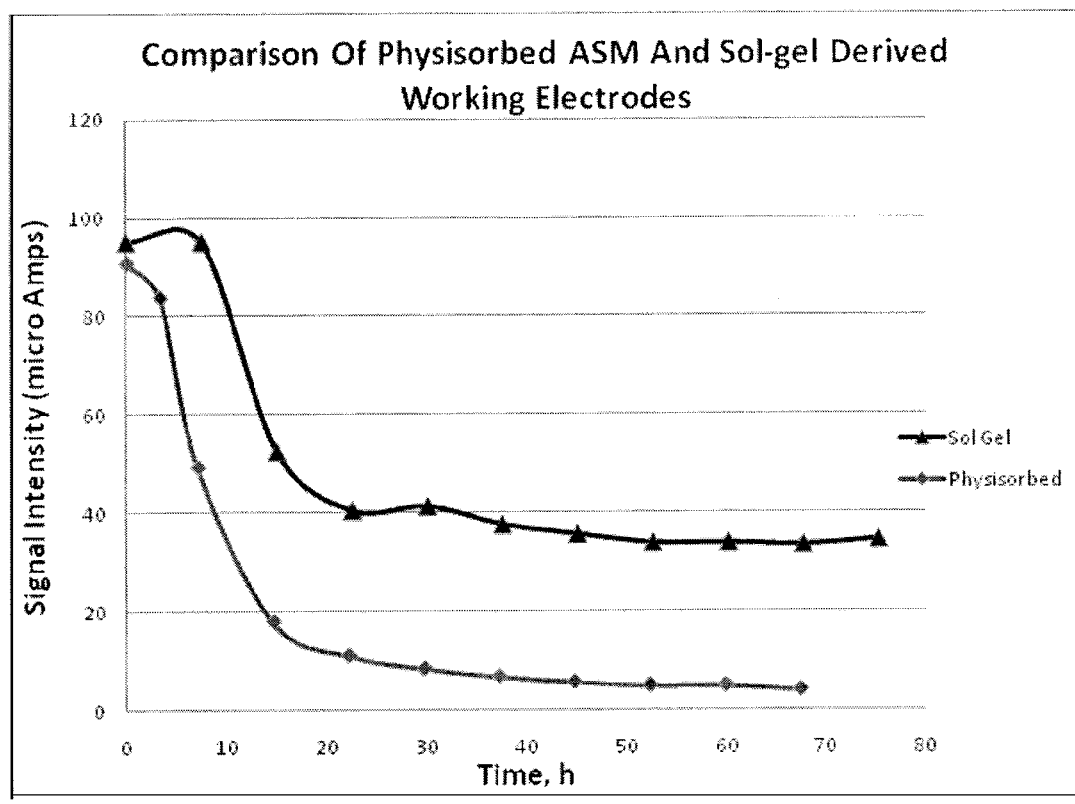
FIG. 1 is a chart demonstrating a comparison of signal sensitivity between physically adsorbed ASM WEs and sol-gel derived WEs in accordance with a representative embodiment of the present invention.

The present invention provides compounds, compositions, methods, electrodes, and sensors, including solid state analyte sensors superior to those currently known in the art. Specifically, in one embodiment, the present invention provides a solid state analyte sensor system incorporating a redox active (analyte sensitive or analyte insensitive) material within a silane-based sol-gel matrix material or an organic polymeric matrix material. Accordingly, some embodiments of the present invention provide improved analyte-dependent signals exhibiting more well-defined peaks, greater peak position stability, higher peak intensity, increased peak longevity, and longer useful lifetime for the electrode construct, relative to currently available analyte sensor systems. Some embodiments of the sensor components, as well as configurations and compositions of those components, are described in detail below, following definitions provided for the convenience of the reader.

DEFINITIONS

As used in the specification and the appended claims, the singular forms "a," an and "the" include plural referents unless the context dictates otherwise. Thus, for example, reference to "a binder" includes mixtures of binders, and a reference to a conductive material may include more than one such binder.

"Alkanyl" refers to a saturated branched, straight-chain or cyclic alkyl group. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, and the like.

"Alkoxy" by itself or as part of another substituent refers to a radical —OR$_{100}$ where R$_{100}$ represents an alkyl group as defined herein. Representative examples include, but are not limited to, methoxy, ethoxy, propoxy, butoxy, and the like.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2- yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. The expression "lower alkyl" refers to alkyl groups comprising from 1 to 8 carbon atoms.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, butynyls such as but-1-yn-1-yl, but-1-yn-3-yl, but-3-yn-1-yl, and the like.

An "analyte" is a chemical species of interest present in a sample, the presence of which is detectable or the concentration of which is measurable by using an analyte sensor system that incorporates a working electrode.

An "analyte insensitive electrode" (AIE) is a special case of a reference electrode where the current flow depends in part on redox processes that are independent of the presence or concentration of species (apart from a minimum threshold of supporting electrolyte) in the sample composition including but not limited to the analyte. The AIE serves to provide a response that does not vary across time or sample composition and therefore can be used as an internal standard or 'zero point' to which the WE response may be compared. See PCT Pub. No. 2010/104962, incorporated herein by reference. An AIE contains one or more ASMs or AIMs in electrical contact with a conductive substrate, a pseudo reference electrode (PRE) as defined below, and a means to place the ASM or AIM and the PRE in a constant chemical environment isolated from, but in electrical and fluid communication with, an analyte solution. As used herein, AIE refers to the integrated functional unit (ASM or AIM, PRE, and other components of the AIE), although it will be clear from the context that, in some of these references, the matrix material component is the subject of the disclosure.

An "analyte-insensitive material" or "AIM" is a redox-active material that is insensitive or substantially insensitive to the presence or the concentration of an analyte in a sample. "Substantially insensitive" to an analyte is used to mean insensitive within the tolerances required for a given application, as those tolerances are defined by an end user.

An "analyte sensing device" is a sensor, a means to measure the signal from the sensor, and optionally a means to display that signal. A pH meter is a type of analyte sensing device. Thus, in some embodiments, an analyte sensing device includes a controller/processor unit, associated programs and algorithms, and a probe.

An "analyte-sensitive material" or "ASM" is a redox-active material that is sensitive or substantially sensitive to the presence or concentration of an analyte in a sample within those user-defined application-specific tolerances. "Substantially sensitive" to an analyte is used to mean sensitive within the tolerances required for a given application, as those tolerances are defined by an end user. An ASM can function as an AIM by sequestration in a suitable ionic medium, as in an AIE.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. The aryl group may be, for example, $(C_5-C_{14})$ aryl, including but not limited to $(C_5-C_{10})$. Illustrative aryls include cyclopentadienyl, phenyl and naphthyl.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In preferred embodiments, the arylalkyl group is $(C_6-C_{20})$ arylalkyl, e.g., the alkanyl, alkenyl or alkynyl moiety of the arylalkyl group is $(C_1-C_6)$ and the aryl moiety is $(C_5-C_{14})$. Illustrative embodiments include the arylalkyl group $(C_6-C_{13})$, e.g., the alkanyl, alkenyl or alkynyl moiety of the arylalkyl group is $(C_1-C_3)$ and the aryl moiety is $(C_5-C_{10})$.

"Coaxial" refers to a common axis about which various components, for example, electrodes, are positioned. In some embodiments, "coaxial" refers to a radial symmetry of concentrically or approximately concentrically positioned components. In some embodiments, the term "coaxial" refers to one or more electrodes being concentrically positioned within an outer or externally positioned electrode component; for example and without limitation, a WE, CE, and RE are coaxially positioned when the CE is the outer ring of a sensor tip that is immersed in the analyte solution, the WE is in the middle of the tip, and the RE is interposed between CE and the WE. See PCT Pub. No. 2010/111531, incorporated herein by reference.

A "counter-electrode" or "CE," also sometimes referred to as an "auxiliary electrode" is an electrode that is required, in some analyte sensors, to pass current through the cell to complete the electrical circuit. This electrode simply serves as a source or sink of electrons and allows current to flow through the WE to effect the redox reaction. To avoid unwanted electrochemical redox processes occurring at the CE, which may interfere with the signal measured at the WE, CEs are typically made using relatively chemically inert materials, commonly platinum (Pt), but carbon allotropes are also commonly employed.

"Dispersed" or "associated" in reference to a material, means that it is dissolved in a solution or colloidally suspended in a gas, liquid or solid. The term also encompasses embodiments in which the material is covalently bound to the surface of a solid or to a component of the solid. The term also encompasses embodiments in which the material is incorporated as a dopant in a crystal lattice. The term also encompasses materials intercalated within a solid.

An "electrode" is a component of a probe.

A "pseudo-reference electrode" (PRE) refers to a type of reference electrode that has traditionally been used in non-aqueous electrolytes. These electrodes typically do not comprise both halves of a redox couple and are therefore not well-defined reference electrodes of fixed composition and potential. However, they provide a reasonably constant potential over the timescale of an electrochemical experiment (on the order of minutes), and the absolute potential of the PRE can then be calibrated back to a RE if required. One example of a PRE is a silver wire (used commonly in non-aqueous electrochemistry). More recently, PREs have been used as a component of an AIE.

A "redox-active material" is a compound or composition that may be oxidized and reduced. "Redox activity" refers to either or both of those processes.

A "reference electrode" (RE) is an electrode used to establish the potential difference applied to the WE. Conventional REs have a certain fixed chemical composition and therefore a fixed electrochemical potential, thus allowing measurement of the potential difference applied to the WE in a known, controlled manner. An RE typically comprises two halves of a redox couple in contact with an electrolyte of fixed chemical composition and ionic strength. Because both halves of the redox couple are present and the composition of all the species involved is fixed, the system is maintained at equilibrium, and the potential drop (i.e., the measured voltage) across the electrode-electrolyte interface of the RE is then thermodynamically fixed and constant. For example a commonly used RE system is the Ag|AgCl|KCl system with a defined and constant concentration of KCl. The two half-cell reactions are therefore: $Ag^+ + e^- \rightarrow Ag$; and $AgCl + e^- \rightarrow Ag + Cl^-$. The overall cell reaction is therefore: $AgCl \rightarrow Ag^+ + Cl^-$ for which the Nernst equilibrium potential is given as: $E = E_0 - (RT/F)*\ln[Cl^-]$, where E is the measured RE potential, $E_0$ is the standard potential of the Ag|AgCl couple vs. the standard hydrogen electrode with all species at unit activity (by convention the standard hydrogen electrode is defined as having a potential of 0.0V); and R, T, and F are the universal gas constant, temperature, and Faraday constant, respectively, in appropriate units. Hence, the potential of this system depends only on the concentration (more strictly speaking the activity) of $Cl^-$ ion present, which, if this is fixed, provides a stable, fixed potential. Many other RE systems are known in the art. It is imperative that the composition of the RE remains constant, and hence almost no current should be passed through the RE (otherwise electrolysis will occur and the composition of the RE will change), which necessitates the use of a third electrode, the counter electrode (CE), to complete the circuit. However, two-electrode configurations can be used in the special case where the WE is a microelectrode, having at least one dimension typically smaller than 100 micrometers. In this case, the currents passed at the WE are small, and therefore a two-electrode cell can be used with a RE, but without the need for a CE.

A "probe" refers to a sensor that contains multiple electrodes. A probe can include, for example, a working electrode, a counter-electrode and a reference electrode (either a conventional reference electrode or a pseudo reference electrode). A probe can include, for example, a working electrode, a counter electrode and an analyte-insensitive electrode.

A "sensor" is an electrode or collection of electrodes that generate a signal in response to the presence of an analyte.

A "surface" of an electrode refers to the functional surface, i.e., that portion of the surface that is in contact with the analyte sample and serves an electrical or electrochemical purpose. It would not, for example, include an insulating WE housing through which no current or voltage passes. The surface of a WE is the portion of the electrode surface in contact with the sample that detects current or electrical potential relative to the RE. The surface of a CE refers to the portion in contact with the sample which serves to deliver or accept current to or from the WE.

A "working electrode" or "WE" is the electrode at which the electrochemical process for detecting the analyte of interest occurs. In a sensor, the working electrode may be sensitive to one or more analyte(s) in the test sample, or it may be chemically modified with analyte sensitive species/materials. The electrochemical response of the working electrode is measured after some perturbation to the system under study has been applied. For example, the perturbation may be the application of a potential difference to the WE which induces electron transfer to occur, and the resulting current at the WE is then recorded as a function of the applied potential (voltammetric mode). This example of mode of operation is illustrative and not exhaustive, as many other modes are known in the art. The WEs of the invention contain an ASM that can undergo a reversible electrochemical redox reaction dependent upon the concentration of analyte (hydrogen ions for a pH meter; other analytes for other analyte sensing devices) in a sample solution and an applied electrical potential. For example, where there is a high concentration of hydrogen ions present in a sample solution, the redox reaction occurs at a lower potential. Conversely, where there is a low concentration of hydrogen ions present in a sample solution, the redox reaction occurs at a higher potential. The relationship between these characteristic potentials and the sample solution pH is a function of the chemical identity of the ASM. An algorithm converts electrical potential to pH value to provide a means of determining the pH of an unknown sample.

With the above definitions in mind, the reader can better appreciate the various aspects and embodiments of the invention described below.

In one important aspect, the present invention provides working electrodes for use in analyte sensing devices and matrix materials for those WEs. In some embodiments, the matrix material of the current invention comprises an ASM covalently attached to a mechanically and chemically stable matrix material. In some embodiments, the matrix material is attached to the substrate surface. In other embodiments, the matrix material alone serves as the electrode (i.e.: there is no substrate). In many embodiments, the matrix material is in the form of a surface coating (composed of a sol-gel or other polymeric material) on a conductive substrate, which together form a WE or AIE. In the case of a WE, the matrix material in this embodiment functions to attach the ASM covalently to a solid structure (the conductive substrate), offer unhindered access of the analyte sample to the ASM, and provide efficient electrical connection between the ASM and the conductive substrate. In some embodiments, the matrix material contains more than one ASM which differ in the potential at which the respective ASMs sense the analyte. The advantage of this multiple ASM system is the greater degree of precision and accuracy associated with multiple data points being taken in the same measurement. Another advantage of this multiple ASM system is its ability to maintain accurate sensing of the analyte concentration even if certain components of the test sample interfere with the normal response of one of the ASMs.

Further, in some embodiments, the present invention provides a matrix material (a sol-gel or polymeric material) that contains both an ASM and an analyte insensitive molecule (AIM). The advantage of this system is that a separate reference electrode is unnecessary in the system, because the signal derived from the AIM is used for the point of reference. As with the WE described immediately above, in some embodiments of this electrode, the matrix material contains multiple ASMs as well as one or more AIMs. The advantages to this system include a greater degree of precision and accuracy associated with multiple data points being taken, as well as obviating the need for a reference electrode in the system.

Further, in some embodiments, the present invention provides a matrix material (a sol-gel or other polymeric material) that contains one or more AIMs and/or one or more ASMs in a suitable electrical environment such that the resulting electrode functions as an AIE.

Suitable ASM materials may include, for example and without limitation: pH sensitive ASMs: anthraquinone (AQ), phenanthrenequinone (PAQ), N,N'-diphenyl-p-phenylenediamine (DPPD), anthracene, naphthaquinone, para-benzoquinone, diazo-containing compounds, porphyrins, nicotinamides, including NADH, NAD and N-methylnicotinamide, quinone thiol, monoquaternized N-alkyl-4,4'-bipyridinium, RuO, and Ni(OH)$_2$, and derivatives of those compounds; CO-sensitive ASMs: ferrocenyl ferraazetine disulfide; alkaline metal cation sensitive ASMs: 1,1'-(1,4,10,13-tetraoxa-7,1-diazacyclooctadecane-7,16-diyl dimethyl), ferrocenyl thiol, other ferrocene derivatives containing covalently attached cryptands, and certain metal complexes with $Fe^{2+}/Fe^{3+}$, $Co2^+/Co3^+$, $Cu^+/Cu2^+$. Suitable ASMs are described, for example, in Hammond, et al., J. Chem. Soc. Perkin. Trans. 707 (1983); Medina et al., J. Chem. Soc. Chem. Commun. 290 (1991); Shu and Wrighton, J. Phys. Chem. 92, 5221 (1988), and PCT application no. PCT/US10/28726. Illustrative examples include the above ferrocenyl ferraazetine and ferrocenyl cryptands, in which an ordinarily chemically insensitive redox center (ferrocene) is covalently linked to a chemical recognition site in such a way as to make its redox potential chemically sensitive. Also suitable are molecules or polymers in which the sensor and reference functionalities are covalently linked such as 1-hydro-1'-(6(pyrrol-1-yl) hexyl-4,4'-bipyridinium bis(hexafluoro-phosphate), as described by Shu and Wrighton, J. Phys. Chem. 92, 5221 (1988).

In some embodiments, the WE comprises two or more ASMs sensitive to the same analyte species, which are selected so as to provide a more sensitive measurement than is provided by a single ASM while minimizing the possibility of introducing additional overlapping peaks which must be resolved to determine analyte concentration. In some examples of this embodiment, the WE comprises both phenanthrenequinone (PAQ) and anthraquinone (AQ). In other embodiments, the WE comprises two or more ASMs sensitive to the same analyte species. Such ASMs could be selected to ensure that not all of them are equally susceptible to potentially interfering species that may be present in a test sample. Compounds such as benzalkonium chloride, a quaternary ammonium chloride, may adversely interfere with ASMs such as AQ and PAQ, for example. An ASM less susceptible to such interference may be for example a derivative with one or more functional groups that sterically or ionically hinder the approach of an interfering species. Alternatively, an ASM can be covalently attached to a matrix material that provides such hindrance.

In other aspects, the WE may further comprise an AIM as an internal standard, as described above. Still further, in some embodiments the WE comprises two or more ASMs, each ASM being selected for sensitivity to a different analyte species.

In one aspect, the present invention provides a matrix material and corresponding electrodes, probes, pH meters and other analyte sensing devices in which an ASM (and/or AIM) is covalently attached to a matrix material prepared from a silane-modified ASM (and/or AIM) precursor and alkoxysilanes using a sol-gel process. Sol-gel processing is a technique often used in materials science that transforms a colloidal solution (sol) to an integrated network matrix material (gel). The resulting matrix material exhibits certain characteristics of ceramic and glass, as well as the pH-responsive functionality (in the case where the redox active material is an ASM selected for use in a WE to be used in a pH sensor) required in a pH sensor. Preparation of these matrices can involve the following illustrative compounds, compositions, and methods of the invention below.

In a first step, a silane precursor with the general structure of Formula (I), below, or salts, hydrates and/or solvates thereof, is synthesized:

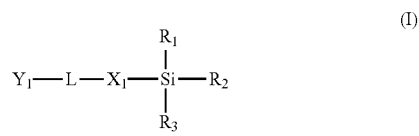

wherein: at least two and typically all three $R_1$, $R_2$ and $R_3$ are independently alkoxy or aryloxy, and if only two are alkoxy or aryloxy the third may be alkyl or aryl; $X_1$ is —O— or a chemical bond; L is a linker; $Y_1$ is —$CO_2H$, halogen, —OH, —$NHR_4$, —$SO_2H$, —$R_5CO$, —$P(O)(OR_6)(OH)$, —$N_3$ or —CN; $R_4$, $R_5$ and $R_6$ are independently hydrogen, alkyl, or aryl. The composition of the silane-modified ASM precursor, including the nature of the -L-linkage, determines the electrochemical response, longevity, and chemical resistance of the resulting electrode and sensor containing the electrode.

Generally, $X_1$ can be any kind of chemical functionality that can form a covalent bond with silicon, and many such functionalities are known to those of skill in the art. In some embodiments, $X_1$ is simply a chemical bond. Connected to $X_1$ is a linking moiety of the formula $Y_1$-L, where L is a linker and $Y_1$ is a linking group. The nature of linker L and linking group $Y_1$ can, as will be appreciated by those of skill in the art upon contemplation of this disclosure, vary extensively. The linker L may be hydrophilic or hydrophobic, long or short, rigid, semirigid or flexible.

A wide variety of linkers L comprised of stable bonds suitable for spacing linking groups such as $Y_1$ from the silicon group are known in the art, and include, by way of example and not limitation, alkyl, aryl, arylalkyl, polycyclic aryls, esters, ethers, polymeric ethers and the like. Thus, linker L may include single, double, triple or aromatic carbon-carbon bonds, etc. Further, alternative embodiments of L include branched structures that influence the spatial configuration of the ASM, including orientation, distance from the sol gel network, the flexibility of the linkage, and/or electron transfer efficiency. In some embodiments, L is a conjugated system or multiple conjugated systems.

Choosing a suitable linker will be within the capabilities of those having skill in the art upon contemplation of this disclosure. For example, where a rigid linker is desired, L can be a rigid polyunsaturated alkyl or an aryl, biaryl, etc. Where a flexible linker is desired, L can be a flexible saturated alkanyl. Hydrophilic linkers can be, for example, polyols (polyalcohols), such as poly(vinyl alcohol) and its derivatives, or polyethers, such as polyalkyleneglycols. Hydrophobic linkers can be, for example, alkyls or aryls.

Alternative embodiments of L include alkyl, aryl, allyl, ether, esters alkoxyl, amide, sulfonamide, and other linkages, including heterocyclic, linear, cyclic, acyclic, or mixed conjugated linkages. The linking group $Y_1$ should be capable of mediating formation of a covalent bond with a complementary reactive functionality of an ASM to provide an isolated silane-modified ASM precursor of the invention. Accordingly, linking group $Y_1$ can be any reactive functional group known to be suitable for such purposes by those of skill in the art upon contemplation of this disclosure. $Y_1$ can be for example, a photochemically activated group, an electrochemically activated group, a free radical donor, a free radical acceptor, a nucleophilic group or an electrophilic group. However, those of skill in the art will recognize that a variety of functional groups that are typically unreactive under certain reaction conditions can be activated to become reactive. Groups that can be activated to become reactive include, e.g., alcohols, carboxylic acids, including salts thereof.

Thus, in some embodiments, $Y_1$ is —$CO_2H$, halogen, —OH, —$NHR_4$, —$SO_2H$, —$R_5CO$, —P(O)(O$R_6$)(OH), —$N_3$ or —CN. In other embodiments, $Y_1$ is —$CO_2H$, halogen, —OH, —$NHR_4$ or —$N_3$ Some embodiments of $Y_1$-L include for example, compounds where L is $(CH_2)_n$—, n is an integer between 1 and 8, $Y_1$ is $CO_2H$, halogen, —OH, —$NHR_4$, —$SO_2H$, —$R_5CO$, —P(O)(O$R_6$)(OH), —$N_3$ or —CN. In some embodiments, $Y_1$ is —$CO_2H$, halogen, —OH, —$NHR_4$ or —$N_3$. In some embodiments, L is —$(C_2H_2)_n$— where n is an integer between 1 and 24.

In some embodiments, $R_1$, $R_2$ and $R_3$ are independently alkoxy, L is —$(CH_2)_n$, $X_1$ is a chemical bond, $Y_1$ is —$CO_2H$, halogen, —OH, —$NHR_4$ or —$N_3$ and n is an integer between 2 and 6. In other embodiments, the silane precursor has the structure of Formula (II):

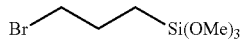

(II)

In still other embodiments, the silane precursor has the structure of Formula (III):

(III)

A wide variety of conventional methods may be used to prepare the silane precursors above and well within the ambit of the skilled artisan. For example, nucleophilic displacement of a silyl chloride (i.e., Cl—Si$R_1R_2R_3$) with $Y_1$L-M or $Y_1$-L-O-M where M is a metal may provide the silane precursors above.

In a second step, an ASM (or AIM) group is attached to the silane precursor to provide an ASM (or AIM) silane precursor of the invention of Formula (IV) depicted below (ASM1 is also represented herein as $ASM_1$):

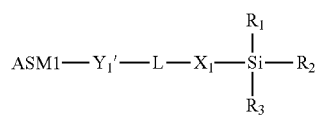

(IV)

wherein: at least two and typically all three $R_1$, $R_2$ and $R_3$ are independently alkoxy or aryloxy, and if only two are alkoxy or aryloxy the third may be alkyl or aryl; $X_1$ is —O— or a chemical bond; L is a linker; $Y_1'$ is —$CO_2NR_4$—, —O—, —$NR_4CO$—, —$SO_2$—, —$R_5CO$—, —P(O)(O$R_6$)O—, —$CO_2$—, —$O_2C$—, —$NR_4O_2$—, —$O_2CNR_4$, —N=N— or a chemical bond; ASK is an analyte sensitive material (or analyte insensitive material, or a derivative of either); and $R_4$, $R_5$ and $R_6$ are independently hydrogen, alkyl, or aryl. In general, ASK is considered a derivative of an ASM (or AIM), because, in the structure of Formula (IV), it differs from the corresponding ASM (or AIM) by loss of a hydrogen atom as necessitated by formation of a covalent bond to either $Y_1$ or L. In some embodiments, $R_1$, $R_2$ and $R_3$ are independently alkoxy; L is —$(CH_2)_n$, $X_1$ is a chemical bond; $Y_1'$ is —$CO_2NH$, or —O—, or —$NHR_4$; and n is an integer between 2 and 6.

In some embodiments, ASK is selected from the group consisting of Formulas (V), (VI), (VII) or (VIII):

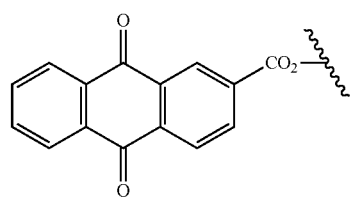

(V)

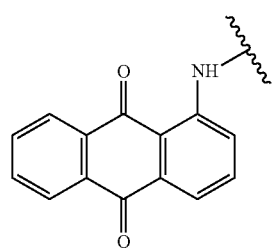

(VI)

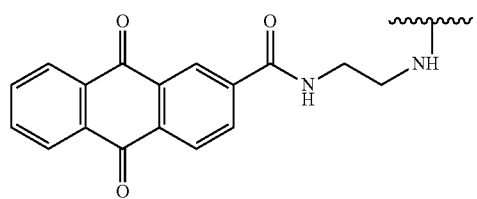

(VII)

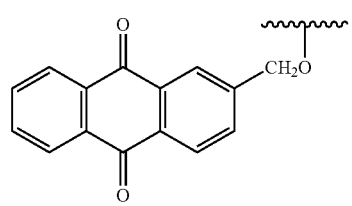

(VIII)

In other embodiments, ASK is derived from an ASM selected from a group consisting of Formulas (IX), (X), (XI), (XII), (XIII), (XIV), (XV) and (XVI):

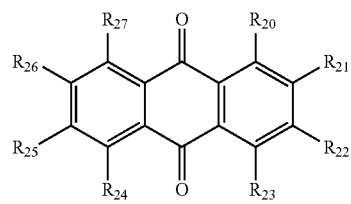

(IX)

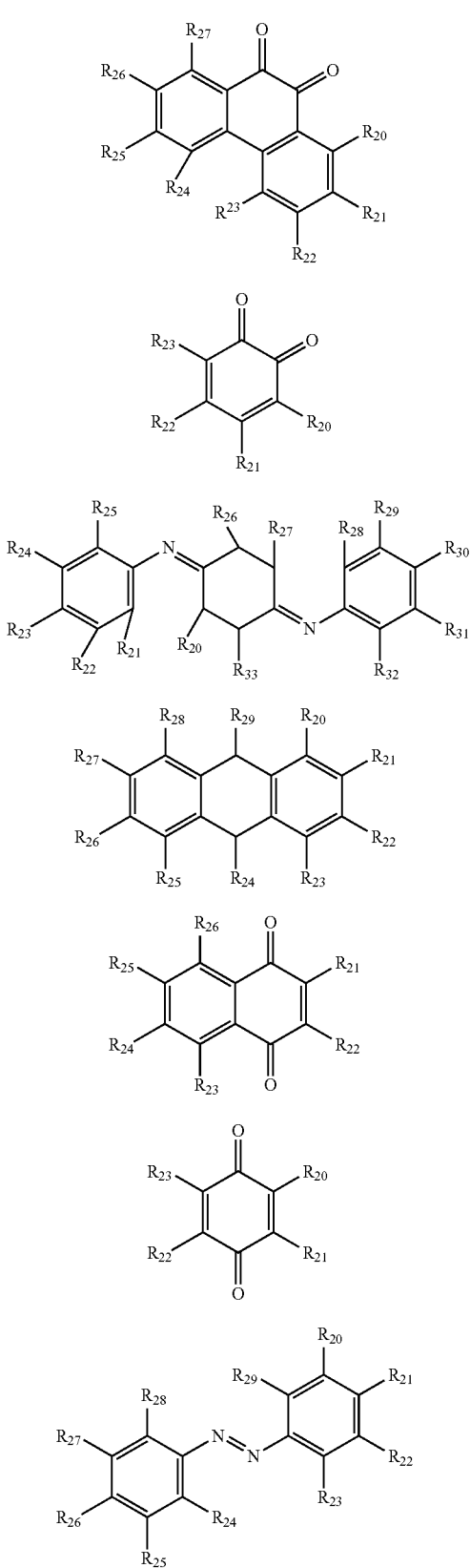

wherein $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$ and $R_{33}$ are independently hydrogen, —CO$_2$H, halogen, —OH, —NHR$_4$, —SO$_2$H, —R$_5$CO, —P(O)(OR$_6$)(OH), —N$_3$, —CN, alkyl, aryl or alkoxy with the proviso that least one substituent is —CO$_2$H, halogen, —OH, —NHR$_4$, —SO$_2$H, —R$_5$CO, —P(O)(OR$_6$)(OH), N$_3$ or —CN.

In some embodiments, the ASM silane precursor of the invention has the structure of Formula (XVII):

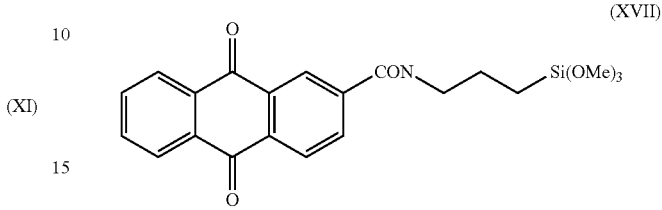

For clarity, the CON in the preceding structure is a carbonyl group linked to a N (the N thus has a hydrogen attached to it that is not shown in the structure). In other embodiments, the ASM silane precursor of the invention has the structure of Formula (XVIII):

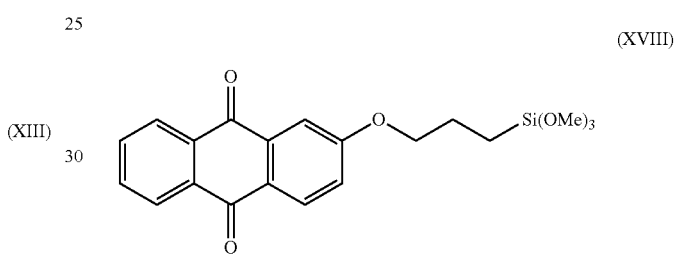

Still, in other embodiments, the ASM precursor of the invention, suitable for use in PVA-derived matrices as described in Example 10, has the structure of Formula (XIX) below, wherein n is 1 or greater than 1:

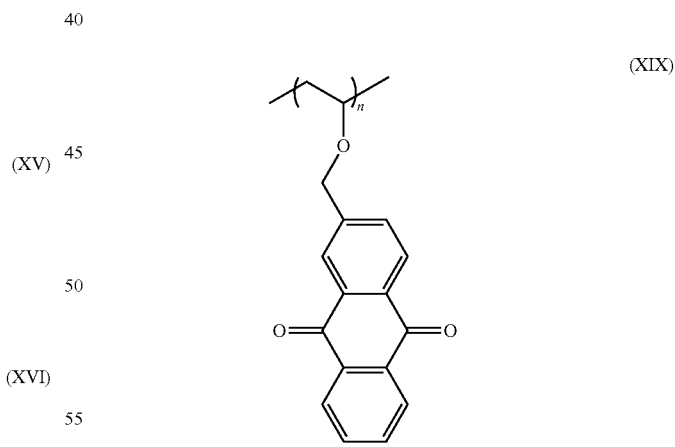

Generally, the ASM silane precursor of Formula (IV) can be assembled from the silane precursor of Formula (I) and an appropriately functionalized ASM using conventional methods of organic synthesis. These include, for example, ester, amide, and sulfonamide condensations, alkylations, 1-3 dipolar cycloadditions, and carbene, nitrene and free radical additions between complementarily functionalized compounds of Formula (I) and ASMs. Thus, the invention also provides new compounds that are complementarily functionalized ASMs suitable for use in such synthetic methods.

In a third step a sol comprising the ASM precursor, a polyalkyl orthosilicate or similar multifunctional silane, solvents, an acid catalyst, and optionally other additives is prepared. At this point, the silane groups in the ASM precursor and the polyalkyl orthosilicate or similar multifunctional silane hydrolyze and undergo crosslinking, converting sol to gel. The resultant sol-gel is heterogeneous to some degree, comprising both liquid and solid regions whose morphologies can range from discrete particles to continuous structures of varying porosities. In the process, the ASM is also incorporated into the crosslinked network to form a matrix of the invention, as shown in the following reaction scheme:

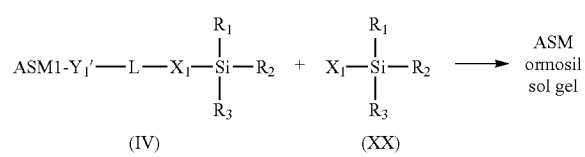

The term "ormosil" stands for "organically modified silica/silicate." In the scheme above, at least two and typically all three $R_1$, $R_2$ and $R_3$ are independently alkoxy or aryloxy, and if only two are alkoxy or aryloxy, the third may be alkyl or aryl. Each of these moieties is independently selectable. Thus, if $R_1$ in Formula (IV) is methoxy, $R_1$ in Formula (XX) can be aryloxy or another alkox, and if $R_2$ and $R_3$ in Formula (XX) are alkoxy or aryloxy, then $R_1$ in Formula (XX) can be alkyl or aryl, even if $R_1$ in Formula (IV) is methoxy. Typically, in compounds of Formula I, Formula (IV), and Formula (XX), at least two and often all three of $R_1$, $R_2$ and $R_3$ are independently methoxy or ethoxy. Following formation of the sol-gel, a coating of this material, which is still in liquid form, is applied onto a prepared conductive substrate. Finally, solvents are removed under controlled thermal treatment conditions which results in a stable structure with ASM covalently bonded to, and dispersed throughout, the matrix material which is substantially in contact with the conductive substrate, thereby forming an electrode of the invention. Thus, the matrix is the analyte (e.g. pH)-sensitive surface of a working electrode of the invention, or is itself formed into the electrode (in those embodiments where no conductive substrate is employed, but the matrix material itself is conducting). If an AIM is used as ASM1, then the matrix serves as the active surface of the AIE, or is itself formed into the electrode (in those embodiments where no conductive substrate is employed, but the matrix material itself is conducting).

Those skilled in the art will recognize that this method may be used to create sensors containing one or more ASMs, one or more AIMs, and combinations of ASM(s) and/or AIM(s). Such combinations can provide additional response signals that vary with analyte identity and concentration, and/or reference signals substantially unchanged with analyte identity and concentration. Such combinations are therefore within the scope of the present invention.

In some embodiments, the sol-gel matrix material comprises a single ASM (or a single AIM). For example, some embodiments of single ASM pH WEs comprise a sol-gel matrix material in which the ASM is selected from the group of compounds consisting of 2-carboxy AQ, 2-N-BOCethylene diamine AQ, 5,12-naphthacene quinone, 1-acetyl amido AQ, 2-carboxamido AQ, and 3-carboxamido PAQ. In other embodiments, a single ASM WE comprises a sol-gel matrix material in which the ASM is 2-(beta-naphthol) methylanthraquinone.

In other embodiments, the sol-gel matrix material of the present invention comprises at least two or more ASM (or ASM and AIM) compounds.

Some embodiments of the present invention comprise a sol-gel matrix material having at least one ASM and optionally comprise one or more additional ASMs and/or an AIM(s). Both the ASMs and AIMs include redox-active materials exhibiting reversible redox activity with well-defined cyclic voltammetry methods.

Some embodiments of the present invention may further include a sol-gel matrix material incorporating an AIM component having a redox potential that is substantially insensitive to the chemical medium to which the sensor is introduced. Such AIMs may include, for example and without limitation AIMs selected from the group comprising ferrocene, n-butyl ferrocene, $K_4Fe(CN)_6$, polyvinyl ferrocene, nickel hexacyanoferrate, ferrocene polymers and co-polymers, including ferrocene styrene copolymer and ferrocene styrene cross-linked copolymer, nickel cyclam, and others. Further, non-limiting examples include ferrocenyl thiol, polyvinyl-ferrocene, viologen, polyviologen and polythiophene. Other embodiments include AIMs comprising ordinarily chemically sensitive materials which are chemically isolated, yet in electrical contact with the chemical medium or analyte sample.

In another aspect, an AIM, such as, for example, a substituted ferrocene such as that depicted below as Formula (XXI), is covalently attached to a matrix material prepared from a silane-modified AIM precursor and alkoxysilanes using a sol-gel process.

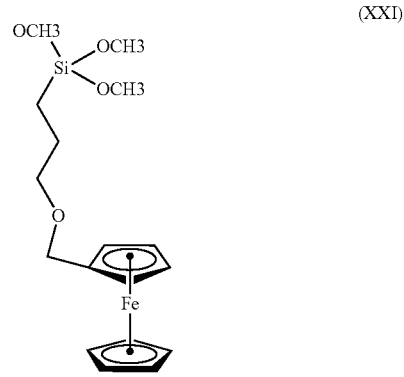

This AIM precursor, and similar AIM precursors featuring alternative linking groups, are compounds of the invention that can be used as the basis of an AIM covalently attached to a matrix material based on the sol-gel chemistry-based methods of the invention. The AIM precursor can be used in admixture with an ASM precursor to form an electrode that produces an analyte-sensitive signal and an analyte-insensitive signal. Alternatively the AIM precursor can be used to form a discrete structure (an AIE) generating a single, analyte-insensitive signal, which can be used in conjunction with an analyte-sensitive signal produced by a co-located WE. In another aspect of the invention, the ASM is covalently attached to a matrix material prepared from a synthetic polymer. The resulting matrix material exhibits both the intrinsic properties of the polymer, which functions as a framework to secure the ASM while offering spatial dispersion for contact between analyte and the ASM, bonding with a conductive substrate, and the analyte (e.g. pH)-responsive functionality required in a WE or the appropriate functionality required for an AIE. Synthetic polymer attributes of interest as ASM matrix materials include, but are not limited to, good film-forming properties, compatibility with conductive substrates, adjustable mechanical properties such as rigidity, strength, ability to be shaped into different form factors, and a wide range of properties attainable by blending, copolymerization, crosslinking, grafting, and physical or chemical modifications at the bulk or surface levels. These attributes permit the design and fabrication of electrodes in sizes, form factors, and performance to meet different requirements. A general approach in some methods of the invention is to use an ASM with suitable functional groups reactive to complementary functional groups in the matrix polymer. Those skilled in the art will recognize, upon contemplation of this disclosure, that the ASM can be situated along the backbone of the matrix polymer and/or on branches or side-chains of the matrix polymer, and that by introducing the ASM as functionalized tethers, crosslinkers, or chain-extenders, a myriad of different matrices of the invention can be prepared.

In yet another aspect, an ASM is incorporated into inherently conductive polymers to derive sensors in which the electrochemical signals generated by the ASM can be efficiently captured and transmitted directly to electronic processing circuits via the conductive polymer. In this aspect, the resulting electrode does not have a traditional conductive substrate. Eliminating the interface between the pH-sensitive matrix material and a separate conductive substrate resolves several problems associated with the physical, chemical, and electronic compatibility of dissimilar materials. The use of polymers, including conductive polymers, helps reduce the complexity and improve design flexibility and manufacturability of electrodes assuming various form factors, and so provides means to fabricate the flexible sensors and miniaturized sensors of the invention.

In some embodiments, a working electrode is prepared using matrix material of the invention based on AQ covalently bound to poly(vinyl alcohol), or PVA. The finished structure comprises an olefinic backbone and an ether-linked side chain to which the AQ moiety is tethered. PVA exhibits excellent resistance to chemical attack, as does the ether linkage connecting the AQ. PVA is also an excellent film-forming polymer. Furthermore, PVA can be crosslinked by chemical and thermal means, further enhancing the dimensional and environmental stability of the finished structure. These are all desirable properties in a pH (or other analyte) sensor expected to encounter a wide range of operating conditions.

In other embodiments, polymers exhibiting good physical, chemical, and mechanical attributes that can be functionalized to attach ASM (or AIM) moieties are generally viable alternatives PVA, and preferred alternatives to PVA for specific applications and/or fabrication methods. Such polymers include, but are not limited to, derivatives of polysulfone, polyethersulfone, polyamides, polysulfonamides, polyimides, polyesters, vinyl polymers, polyphenylene sulfide, polysaccharides, cellulose, derivatives thereof, copolymers thereof, blends thereof, and composites thereof. ASM (or AIM) attachment methods include, but are not limited to, reaction with functionalized ASMs (AIMs), grafting of polymers already containing ASMs (or AIMs) as tethers, interpenetrating networks of multiple polymer or oligomer components in which at least one of the components comprise covalently-attached ASM (or AIM) moieties.

In other aspects of this invention, a combination of a single ASM, a plurality of ASMs, an AIM, and/or a plurality of AIMs, are covalently attached to a matrix material prepared from alkoxysilanes and a silane-modified ASM (or AIM) precursor using a sol-gel process, or covalently attached to a matrix material prepared from an optionally crosslinked polymer.

In some embodiments, the concentration of ASM on the WE (or AIM on the WE or the AIE) is increased by applying multiple layers of ASM (or AIM)-containing sol-gel matrix material or polymeric matrix material to the WE (or AIE) substrate. In accordance with the present invention, the ordinarily skilled artisan can control the amount of pure ASM (or AIM) entrapped within the matrix material onto the substrate, thereby permitting the manufacture of WEs (or AIEs) and probes containing them having a size and shape appropriate to a given application to achieve additional benefits of the invention.

In some embodiments, the WE comprises ASM present in a sufficient amount to result in a pH-dependent signal of between 2 and 300 microamperes. In some embodiments, the size and shape of the WE are chosen so as to minimize deleterious electrochemical effects among the WE, RE and CE (or WE, AIE, and CE) while maintaining WE performance sufficient to allow a user to distinguish the analyte-dependent signal over background noise while maintaining signal quality.

The WEs (and AIEs) of the present invention may be configured so as to be removable from the probe, allowing them to be easily interchanged or replaced according to the required design and functionality. The WEs of the invention can be configured and programmed to replace a traditional glass probe in a traditional pH meter and/or to generate a signal that is transmitted by electrical wiring, or via electromagnetic means not requiring wires, to a readout device (see U.S. provisional patent application Ser. Nos. 61/475,164, filed 13 Apr. 2011, and 61/475,590, filed 14 Apr. 2011, both of which are incorporated herein by reference).

Some embodiments of the present invention further provide improved analyte sensors having one or more WEs, each comprising one or more ASMs entrapped within a sol-gel or other polymeric matrix material and disposed on a substrate and in electrical connection with that substrate.

In some aspects, the WE comprises an AQ derivative as an ASM. In other aspects, the present invention provides a WE that comprises phenanthrenequinone (PAQ) or a derivative thereof as an ASM. Further, in other aspects the present invention provides a WE that comprises ortho-benzoquinone (OQ) or a derivative thereof as an ASM. Still further, in other aspects, the present invention provides a WE that comprises N,N-diphenyl para-phenylene diamine (DPPD) or a derivative thereof as an ASM.

In some aspects, the present invention provides an electrode that comprises anthracene (AC) or a derivative thereof as an ASM. In other aspects, the present invention provides an electrode that comprises naphthoquinone (NQ) or a derivative thereof as an ASM. Further, in other aspects the present invention comprises provides an electrode that para-benzoquinone (PQ) or a derivative thereof as an ASM.

Those of skill in the art will appreciate, in view of this disclosure that, in general, many of the teachings herein that concern ASMs are equally applicable to AIMs.

A variety of substrate materials are suitable for use in the WEs and AIEs of the present invention. These include but are not limited to carbon, carbon allotropes, and derivatives thereof, various carbon-based materials, transition metals, noble metals such as gold and platinum, conductive metal alloys, various conductive polymers and copolymers and compounds and derivatives thereof, polymer blends and polymer composites, semiconductive materials such as silicon and derivatives thereof, including doped silicon and doped semiconductive materials, and additional suitable materials known to those of skill in the art.

In some aspects, the substrate is or comprises carbon. A variety of carbon substrates are suitable for use as substrate material in the electrodes of the present invention, including but not limited to carbon allotropes such as pyrolytic graphite, graphite, amorphous carbon, carbon black, single- or multi-walled carbon nanotubes, graphene, glassy carbon, boron-doped diamond, pyrolyzed photoresist films, and others known in the art. Additionally, all of the above carbon allotropes may be dispersed in powder form in a suitable binder, or formed in-situ on the substrate surface. Such binders include organic or inorganic polymers, and adhesive materials. In some embodiments, the substrate is graphite powder and the binder is epoxy resin. In other embodiments, the substrate is a graphite rod. In other embodiments, the substrate is a carbon fiber composite. In other embodiments, the substrate is a graphite-filled polymer exemplified by, but not limited to, polyphenylene sulfide. In other embodiments, the substrate comprises a surface coating of an ink formulated with one or more carbon allotropes.

Thus, in some embodiments, the substrate comprises a composite material comprising graphite and a binder, such as an epoxy. In some embodiments, the substrate comprises a composite material comprising carbon fibers and one or more binders. In some embodiments, the substrate comprises a conductive polymer such as polyaniline, polypyrrole, or various carbon allotrope-filled polymers, where the polymer components may include, without limitation, polyphenylene sulfide, polyolefins, polyamides, polyimides, polyesters, polysulfone, polyethersulfone, various vinyl polymers, cellulose, poly(amino acids), derivatives thereof, copolymers thereof, blends thereof, and composites thereof. In some embodiments, the substrate comprises materials surface-treated by corona discharge, electron beam, gamma irradiation, plasma, and other forms of irradiation that result in an activated surface by ion or free radical generation. Optionally, such activated surface may be further modified to enable attachment of ASM (or AIM) derivatives or matrix materials containing covalently attached ASM (or AIM) moieties.

In some aspects of the invention, the surface of the substrate is cleaned or otherwise "prepared" prior to applying the ASM (or AIM) containing sol-gel or polymeric matrix material. Suitable methods for graphite/epoxy substrates and other substrates include but are not limited to sanding and/or polishing the surface of the substrate, which may be formed into a plug, followed by directing a stream of pressurized air or other gas onto the substrate surface, and optionally sonicating in a suitable solvent, to dislodge particulates resulting from sanding or polishing. Alternatively, and optionally, the substrate surface may be cleaned with various solvents, alkalis, and/or acids, followed by thorough removal of such cleaning agents by means well known to the skilled practitioner. These methods, applied selectively to substrates compatible with the treatment conditions and chemicals, serve to remove superficial contamination prior to attachment of the ASM (or AIM)-containing matrix material. The resulting WE (or AIE) is capable of rendering an analyte-dependent signal (or appropriate AIE signal) having superior useful lifetime as compared to the signals produced by WEs (or AIEs) in which the ASM (or AIM) is physically adsorbed without employing a matrix material or is covalently attached to the substrate.

A substrate acts as a self-contained entity that serves as a physical and electrical bridging unit between one or more ASMs (or AIMs) within the sol-gel or polymeric matrix material, and an electrical conduit, such as a wire. The physical function of the substrate is to provide a support for the ASM (or AIM) sol-gel or polymeric matrix material such that the electrode may be brought into direct contact with a sample of interest, typically a liquid, safely and conveniently in the form of a probe or a functionally equivalent assembly. The substrate and matrix material thereby allow the ASMs (or AIMs) to interact with the sample of interest. The electrical function of the substrate is to propagate charge carriers such as electrons from the electrical conduit to the ASM (or AIM) to enable a redox reaction. In some embodiments, a substrate material is selected to be chemically inert to the anticipated environments of the sample to be analyzed, and an ability to conduct electrical current with minimal loss.

As discussed above, in some embodiments, the pH or other analyte probe of the invention further includes a reference electrode (RE). A number of reference electrodes suitable for use in a probe of the present invention are known in the art. See, for example, Bard and Faulkner, "Electrochemical Methods: Fundamentals and Applications" (Wiley 2001), incorporated herein by reference.

In some embodiments of the invention, the reference electrode comprises a chloridized silver wire surrounded by an electrolytic solution, as described in the examples below. In other embodiments, the RE comprises only a chloridized silver wire. In other embodiments, the RE comprises an iodide/tri-iodide system as described in U.S. Pat. No. 4,495,050, incorporated herein by reference.

Optionally, "pseudo-reference" (PRE) (sometimes referred to as "quasi-reference") electrodes are used, particularly in non-aqueous electrolytes, in an analyte sensor of the invention. An illustrative but non-limiting example of a PRE is a silver wire, commonly used in non-aqueous electrochemistry; other PREs may be used according to the particular application.

In some embodiments, the surface area of the RE exposed to the analyte sample is selected so as to minimize or eliminate intra-electrode electrochemical effects that adversely affect analyte-dependent signal quality.

The present invention also provides a variety of embodiments in which a solid-state working electrode (WE) featuring a redox-active analyte-sensitive material is operated in conjunction with a conventional RE in the same pH metering system. This hybrid approach combines the robustness inherent in solid-state devices and the accepted reference standard upon which much of electrochemistry science is based.

Thus, one of ordinary skill in the art will appreciate the unique hybrid configuration of various embodiments of the present invention. In particular, one of ordinary skill in the art will appreciate the present combination of a solid-state WE with a conventional RE, typically with a CE as well. This hybrid configuration provides a pH probe assembly having the reliability of a conventional RE without the unwanted and cumbersome calibration requirements of traditional glass working electrode. Thus, the present invention provides new and useful combinations of electrodes that overcome the limitations of traditional pH (or other analyte) probes and metering systems.

In some embodiments the RE is modified to include a miniature reference assembly configured in the shape of the letter "J", as described in PCT Pat. Pub. No. 1010/111531, incorporated herein by reference. The miniature reference electrode is alternatively placed at the proximal end of a traditional RE such that the chloridized silver wire of the miniature reference assembly is positioned adjacent or proximal to the WE of the pH probe. The shape of the miniature reference ensures that at least a portion of the chloridized silver wire is located in close proximity to the sample solution. Thus, the temperature of the wire is substantially similar to the WE, typically within 10% of the temperature of the WE and the analyte solution. In some embodiments, the temperature of the wire varies less than 2 degrees from the temperature of the WE following equilibration of the probe assembly in the analyte-containing sample. In other embodiments, the temperature of the wire varies less than 1 degree from the temperature of the WE following equilibration of the system. Still further, in some embodiments the temperature of the wire varies less than 3 degrees from the temperature of the WE following equilibration. Subjecting the silver wire to substantially the same temperature as the WE and/or sample solution reduces the temperature sensitivity of the sensor thereby increasing the accuracy of the pH probe and meter.

Some embodiments of the present invention are probes that include a counter electrode (CE). In operation, the CE serves as an electron source or sink, thereby delivering current to the sample and allowing it to flow through the pH probe system.

Suitable CEs are known in the art. See, for example, Bard and Faulkner, above. To avoid unwanted electrochemical redox processes occurring at the CE that can interfere with the signal measured at the WE, the CE is typically made of a relatively chemically inert material, commonly stainless steel, carbon (e.g., graphite) or platinum.

In some embodiments, as illustrated in the examples below, the CE is a graphite or carbon-based rod. In other embodiments the CE is a carbon-fiber tube. Still further, in some embodiments the CE is an electrically conductive material, as known in the art.

Various references describe the importance of the WE:CE surface area ratio to sensor performance. In various embodiments of the present invention, the surface area of the CE exposed to the analyte sample is selected so as to minimize or eliminate intra-electrode electrochemical effects that adversely affect analyte-dependent signal quality and longevity, as described herein. In some embodiments, the ratio of the surface area of the CE to that of the WE is from about 1:1 to about 1:10. In other embodiments this ratio is about 1:2, and in further embodiments the ratio is about 1:1.5.

In some embodiments, the CE comprises an electrically conductive carbon-fiber tube having a hollow inner lumen for housing various other components of the pH sensor. The carbon-fiber tube is electrically coupled to a preamplifier module whereby a voltage is applied to the sample solution via the CE. One skilled in the art will appreciate that, in addition to providing electrochemical cell driving potential, the electrically conductive, low-impedance CE serves as an electromagnetic shield to protect components housed within CE, especially the high-impedance RE, from external electromagnetic interference. In some embodiments, a coaxial configuration is implemented whereby an external position of the CE provides electromagnetic shielding to the RE and WE, which electrodes are concentrically or approximately concentrically positioned within the CE. One skilled in the art will further appreciate that the shielding function of the CE is not dependent upon the concentric positioning of the RE and WE. Rather, one skilled in the art will appreciate that the exact positions of the RE and WE may be internally altered relative to the external position of the CE and still receive the shielding protection as discussed above.

In some embodiments, the invention provides an analyte insensitive electrode (AIE) that is used in lieu of a conventional RE.

The AIE is capable of generating a substantially analyte insensitive signal in response to the application of an electrical stimulus applied to the sample being analyzed in the course of making voltammetric or amperometric measurements of analyte concentration in the sample. The AIE provides a predictable signal useful as an internal standard (in other words, a standard internal to the system) with which an analyte-sensitive signal may be continuously compared, and therefore permit greater accuracy and reproducibility in determining analyte concentration.

Thus, in some embodiments of the present invention, an AIE is used in the electrochemical analyte sensing device to generate a substantially analyte-insensitive electrical response when an electrical stimulus is applied to an analyte sample in the course of making voltammetric and/or amperometric measurements of analyte concentration.

The teachings of the current invention regarding different WE chemistries are also applicable to certain embodiments of the AIE. Specifically, an AIE can feature the same pH—(or other analyte-) responsive surface chemistry as the WE and, due to its specially-formulated constant chemical environment and the PRE it contains, used to replace the conventional RE (such as Ag|AgCl|KCl). See PCT Pat. Pub. No. 2010/104962, incorporated herein by reference.

Conventional REs operate by establishing a stable, well-characterized electrode potential. The stability of this electrode potential derives from a redox system with constant activities of each participant of the redox reaction. Stable electrode potentials are obtainable using electrodes with covalently-attached ASM (or AIM) matrix material as the sensing surface. These electrodes generate highly reproducible electrode potentials in a constant chemical environment such as that provided by a buffer solution. Thus, one embodiment of an AIE of the invention contains a redox-active matrix material of the invention, optionally attached to a substrate, and a PRE in a buffer solution contained within an enclosed volume. This enclosed volume is, in turn, in fluid and electrical communication through a liquid barrier such as a porous frit with the analyte solution. In operation, this AIE is co-located with the WE and the CE, and each electrode is in direct contact with the analyte solution. Regardless of whether a redox active material is characterized as an ASM or AIM, it can be made analyte-insensitive by sequestration in a properly formulated ionic medium, as contained in an AIE.

In operation, the AIE exhibits an electrode potential dependent largely on the nature of the redox active material and the nature of the constant chemical environment in which it is sequestered, i.e., in a properly formulated ionic medium (see U.S. provisional patent application No. 61/434,800, filed 20 Jan. 11). Provided that an appropriate liquid barrier is selected, convective mixing between the analyte sample and a properly formulated internal buffer solution can be reduced to insignificant levels on the time scale of interest. Any intrusion of the analyte sample across the liquid barrier will only exert a minimal effect on the chemical environment because of the inherent ability of the buffer solution to mitigate pH shifts due to composition changes. The result is an exceptionally stable electrode potential compared with conventional REs such as Ag|AgCl|KCl, in which the KCl solution has no significant buffering capacity. This fundamental advantage of the AIE over conventional REs, coupled with the stability derived from covalently-attached ASM (or AIM) matrix material, results in unexpectedly superior performance of this new class of pH probes containing such electrodes.

The AIE and the WE function similarly in that both are redox-active electrodes. In one embodiment of a sensor of the invention, the redox-active material and matrix containing it in the AIE and the WE are identical or substantially similar. In another embodiment of the sensor, the AIE and the WE have different chemical compositions, i.e., they differ in the redox-active compound employed or in the matrix employed, or both. The latter embodiments offer additional degrees of freedom and greatly expand the different types of pH (and other analyte) sensing systems of the invention, in that the AIE and the WE may be individually tailored to deliver the most beneficial combination of physical and performance attributes. For example, the WE can be based on a chemical composition designed to offer the highest accuracy over a broad pH range, whereas an alternate WE can be based on a chemical composition designed to withstand aggressive chemical environments such as strong acids or alkalis. In either case, the AIE can be based on a chemical composition exhibiting the highest precision in the presence of a neutral buffer to offer the longest life expectancy for the AIE. The chemistry options described in the present invention, including various linking chemistries, enable control of WE properties to meet these diverse needs.

In various embodiments of the current invention, an AIE featuring constant chemical environments in the form of a semi-solid or a solid are employed. See U.S. provisional patent application No. 61/434,800, filed 20 Jan. 11, incorporated herein by reference. Thus, in one embodiment, the reference solution of the AIE is replaced with a solid (the "reference material") that provides buffering capacity, electrical conductivity, and ionic permeability. The reference material is a hydrophilic solid with sufficient ionic content to serve as a conduit of hydrogen ions in the analyte solution, and a conductor of electrical current between the CE and the AIE. The reference material is in direct contact with the analyte on one side, and with the functional surface of the redox-active material and with the PRE on the other side. In one embodiment, the reference material is selectively permeable to hydrogen ions but substantially impermeable to other entities in the analyte solution, so that the redox-active material within the AIE will not be exposed to a changing chemical environment during use. In another embodiment, an additional liquid barrier is used at the interface between the reference material and the analyte. Such a barrier may be in the form of an ionic liquid or room-temperature ionic liquid. In this way, the AIE overcomes problems associated with maintaining wet reference systems, may be stored dry over long periods until use, and may be kept dry between measurements in analyte solutions, i.e., has wet-dry reversibility.

Suitable reference materials include crosslinked ionic polymers with compositions that mimic those of liquid buffer solutions; for example, a combination of strongly basic and weakly acidic functionality, or a strongly acidic and weakly basic functionality.

The principles and methodologies of the current invention regarding the creation of WEs embodying certain desirable attributes can be applied to various designs of electrodes, probes, sensor assemblies, analyte measuring devices, meters and systems, and instrumentation. Each of these deployments will benefit from the advantages of electrodes of the current invention over conventional electrode systems, in particular those based on glass probes, and specifically glass pH probes.

Thus, in one embodiment of the invention, an amperometric probe is provided for use in conjunction with conventional pH meters as a universal replacement of the glass probe. See U.S. provisional patent application No. 61/475,500, filed 14 Apr. 11, incorporated herein by reference. The amperometric probe described in that application comprises a WE, a RE, and a CE. In other embodiments, the current invention provides a WE, an AIE, and a CE that together replace the probe of a traditional pH meter (or other analyte sensing device), as described in that application.

In yet another aspect, the present invention provides an amperometric probe for measuring pH comprising a probe, signal processing algorithm, and circuitry that enable wired or wireless communication of pH, temperature, and other analyte characteristic information to, and to be processed, analyzed, or displayed by, computing devices. See U.S. provisional patent application No. 61/475,164, filed 13 Apr. 11, incorporated herein by reference. The methods, electrodes, and electrode combinations (e.g. WE, RE, and CE; and WE, AIE, and CE) of the present invention can be used in amperometric probes as described in that application.

For an electrode and corresponding probe to achieve maximal longevity, the peak intensity (the magnitude of the current at its maximum) of the WE should decrease minimally over time. As shown in FIG. 1, the ASM sol-gel WE displayed less signal loss as compared to a WE where the ASM is physically adsorbed on the substrate. While the electrodes and sensors prepared via sol-gel (or other polymer) deposition can initially lose some fraction of their initial signal intensity, as illustrated in the example described in FIG. 1, the signal in this illustrative example stabilizes subsequently at a level with acceptable signal-to-noise ratio. These results are significant, because a decrease in signal loss results in increased detectability and signal-to-noise ratio, and a longer functional lifetime for the WE.

Figure 2:
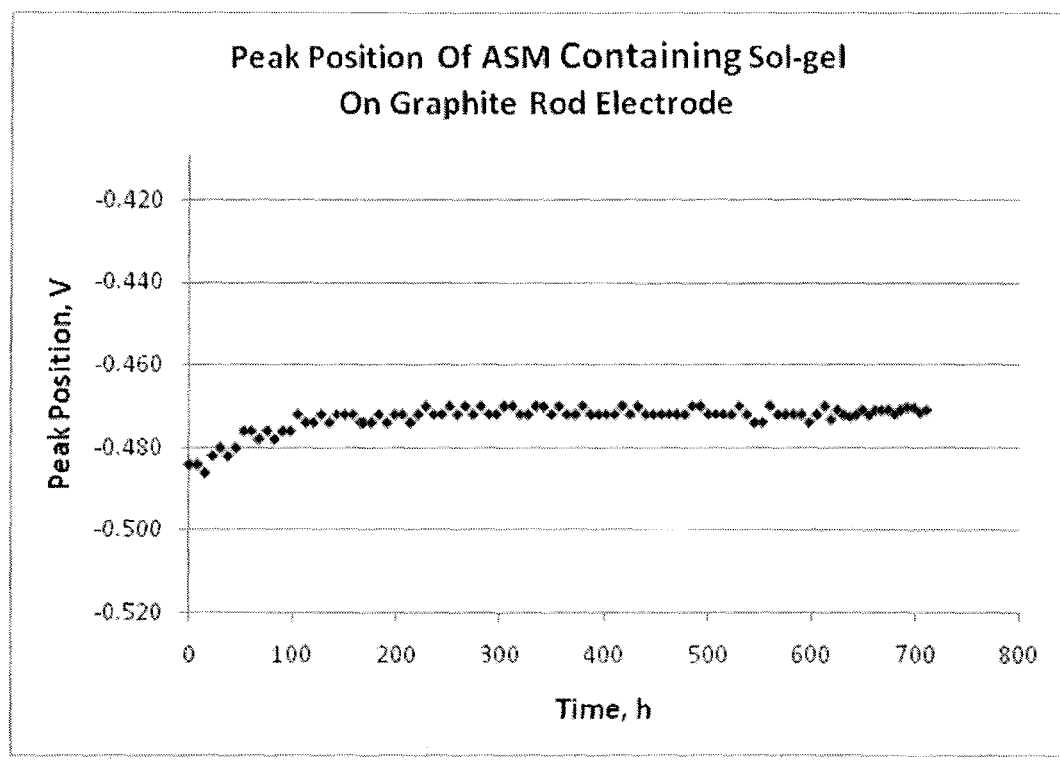
FIG. 2 is a chart demonstrating the peak position of an ASM containing sol-gel derived WE in accordance with a representative embodiment of the present invention.

FIG. 2 illustrates the signal stability over a 30 day lifetime of a WE prepared using the sol-gel deposition method of the invention. In particular, FIG. 2 demonstrates negligible variation of peak position for the ASM sol-gel WE over a 30 day period. Typically, a WE produced using physical adsorption as the mode of ASM/electrode surface interaction provides useable signals only up to about 2 days. For single use and limited use applications, a short useful lifetime may be adequate. However, for applications which demand longer useful lifetimes, such electrodes are inadequate. Thus, the ASM sol-gel (or other polymer matrix) WE (and AIE) of the present invention provides a solution to the problem of short electrode lifetime.

Those of skill in the art will appreciate upon contemplation of this disclosure that there are many alternative ways of implementing and realizing the many benefits and advantages afforded by the various aspects and embodiments present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and do not limit the scope of the invention.

EXAMPLES

Example 1

Synthesis of an Amide-Linked AQ Silane

Synthesis of an amide-linked AQ silane was prepared, as shown in the following reaction scheme:

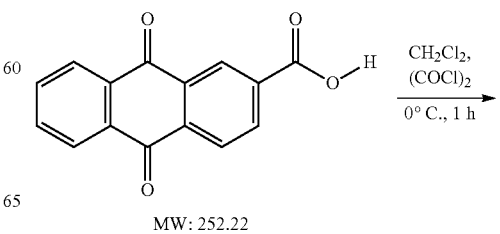

MW: 252.22

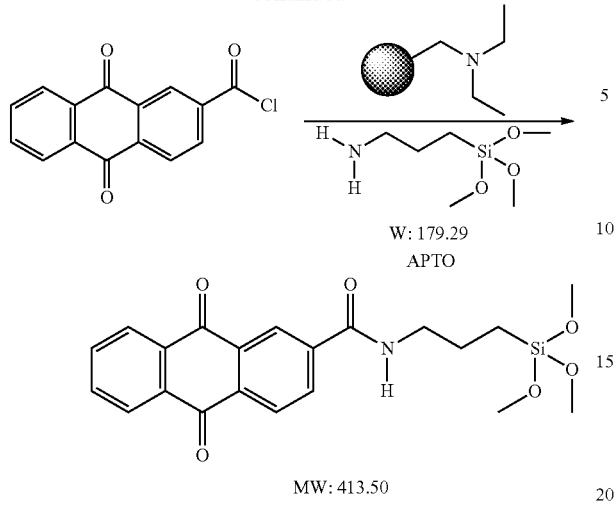

W: 179.29
APTO

MW: 413.50

This example and the following Examples 2 and 3 describe compounds and methods of the invention for making an ASM-amide-linked sol-gel matrix material and corresponding WE of the invention. Anthraquinone-2-carboxylic acid (0.500 g, 1.98 mmol) was suspended in dichloromethane (20 mL) in a vial, and then the vial was purged with nitrogen. 0.2 mL of dimethylformamide (DMF) was added dropwise, followed by addition of oxalyl chloride (0.18 mL, 2.2 mmol). The solution was stirred for 2 h. Then, diethylaminomethylpolystyrene (1.97 g, 6.3 mmol of amine) was added followed by 3-aminopropyltrimethoxysilane (APTOS) (0.37 mL, 2.1 mmol). Stirring was continued for 16 h at ambient temperature. The resultant liquid was filtered to remove the diethylaminomethylpolystyrene solid. Additional dichloromethane was used to rinse the retained solid to recover entrained product. The dichloromethane was removed in a rotary evaporator to obtain an amber oily liquid. Anhydrous alcohol was used to reconstitute the oily liquid to obtain 20 mL of the amide-linked AQ silane solution.

Example 2

Preparation of Amide-Linked AQ Sol-Gel Matrix Material

A preparation of amide-linked AQ sol-gel matrix material was prepared, as shown in the following reaction scheme:

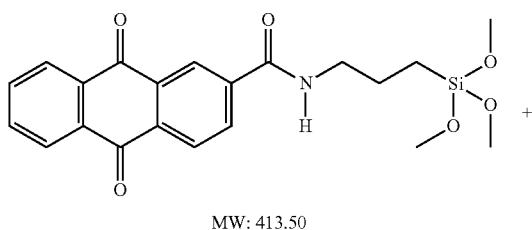

MW: 413.50

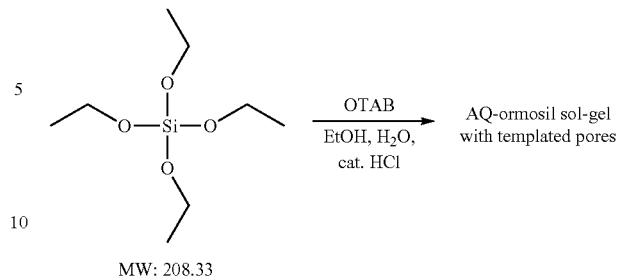

MW: 208.33

A sol was prepared by combining ethanol (3.5 mL), water (0.250 mL, 14 mmol), 0.1M HCl (0.200 mL, ~11 mmol water), and TEOS (1.00 mL, 4.48 mmol) in a 20 mL vial, as shown in the reaction scheme immediately above. The amide-linked AQ silane solution (1.5 mL, 0.01 mmol/mL, 0.015 mmol) was added. The resulting solution was heated at 70° C. with stirring. After 1 h, a solution containing 0.135 g of octyltrimethylammonium bromide (0.53 mmol) and 6.5 mL ethanol was added, and stirring was continued at ambient temperature for 1 hour.

Example 3

Preparation of Amide-Linked AQ Sol-Gel Working Electrode

To prepare the WE, a carbon fiber composite rod of 0.180 in diameter was mounted in a polyetheretherketone (PEEK) surround and sanded until the carbon disk reaches a 0.06 in thickness. These blank substrates are immersed in the sol containing the amide-linked AQ described in the previous paragraph for 30 s, removed from the liquid, and heated in a 150° C. oven for 1 h.

Samples of these working electrodes were tested using an Autolab potentiostat (Metrohm Autolab B.V.) with a pH 7 buffer standard at room temperature, with the results shown in Table1.

TABLE 1

| Sample Code | Peak position (V) | Peak current (µA) |
| --- | --- | --- |
| AA063 | −0.4871 | 36.4 |
| AA096 | −0.4873 | 25.1 |
| AA065 | −0.4871 | 36.4 |
| AA032 | −0.4880 | 27.3 |

Example 4

Synthesis of an Ether-Linked AQ Silane

Synthesis of an ether-linked AQ silane was prepared, as shown in the following reaction scheme:

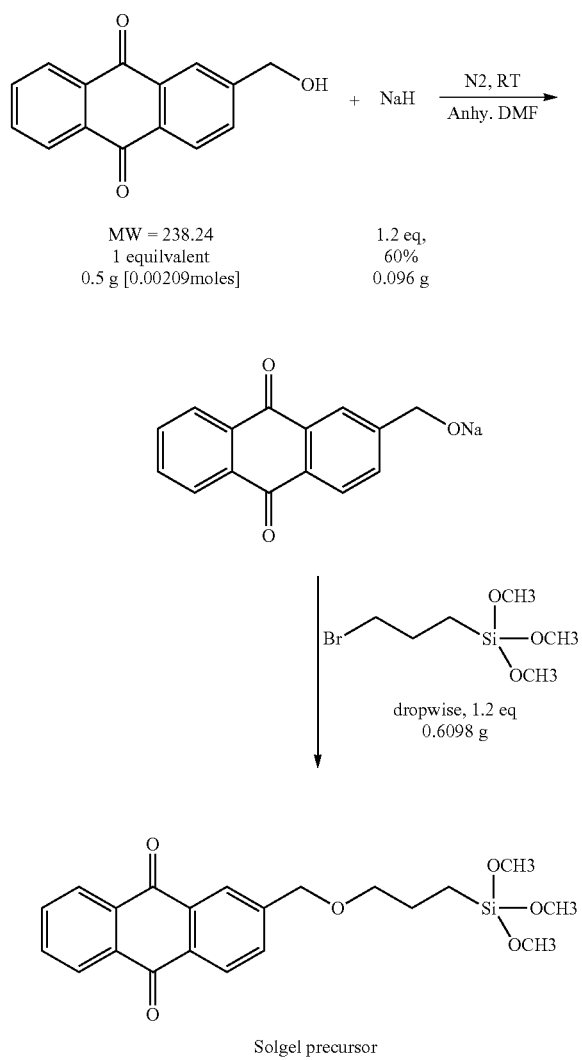

Solgel precursor

This example and the following Examples 5 and 6 describe compounds and methods of the invention for making an ASM-ether-linked sol-gel matrix and corresponding WE of the invention. Sodium hydride [60%, 0.096 g] was slowly added to a clean and dry three neck round bottom flask under a nitrogen atmosphere. Then, 100 ml of anhydrous DMF was added to the flask using a syringe. This mixture was stirred for 30 min. 0.5 g [0.00209 moles] of 2-(hydroxy methyl) anthraquinone was added and stirred until completely dissolved. After 3 h of continuous stirring, 0.6096 g [1.2 eq, 0.6 ml] of (3-Bromopropyl) trimethoxy silane was added dropwise with nitrogen blanketing and stirring. The reaction was conducted at room temperature for 4 days, and then stopped by addition of 10 mL of ethyl acetate, followed by stirring for 1 h. The reaction vessel was opened to air, and the reaction mixture was filtered in a Buchner funnel to remove the salt formed, and the liquid was concentrated in a rotary evaporator to remove ethyl acetate and DMF to obtain the ether-linked AQ silane stock solution.

Example 5

Preparation of Ether-Linked AQ Sol-Gel Matrix Material

A preparation of ether-linked AQ sol-gel matrix material was prepared, as shown in the following reaction scheme:

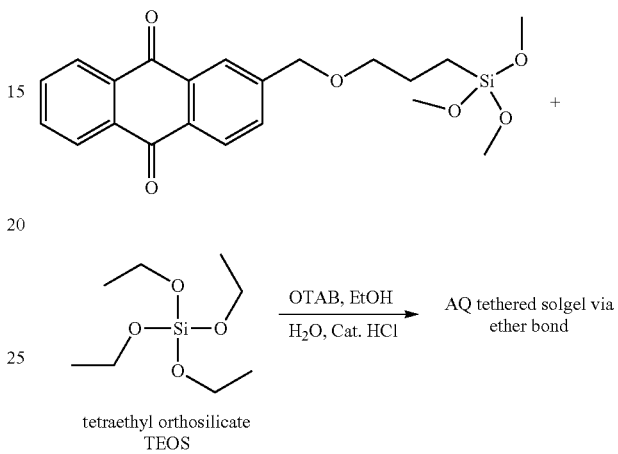

A sol-gel matrix was prepared according to the above reaction scheme as follows: TEOS (1 mL, 5 mmol) was stirred in ethanol (3.5 mL) at 70° C. Water (0.250 mL, 14 mmol) and 0.1M HCl (0.200 mL, ~11 mmol water) were added. Then, 1.5 mL of the ether-linked AQ silane stock solution was added. The combined solution was heated at 70° C. and stirred for 1 h.

Example 6

Preparation of Ether-Linked AQ Sol-Gel Working Electrode

To prepare the WE, a carbon fiber composite rod of 0.180 in diameter was mounted in a PEEK surround and sanded until the carbon disk reaches a 0.06 in thickness. These blank substrates were immersed in the sol containing the ether-linked AQ described in the previous paragraph for 30 s, removed from the liquid, and heated in a 150° C. oven for 1 h. Samples of these working electrodes were tested on an Autolab potentiostat with a pH 7 buffer standard at room temperature, with the results shown in Table 2.

TABLE 2

| Sample Code | Peak position (V) | Peak current (μA) |
|---|---|---|
| AA014 | −0.503 | 16.6 |
| AA020 | −0.505 | 16.1 |
| AA042 | −0.501 | 19.5 |
| AA055 | −0.505 | 24.4 |

Example 7

Synthesis of an Ether-Linked Ferrocene Silane

This example and the following Examples 8 and 9 describe compounds and methods of the invention for making an AIM-amide-linked sol-gel matrix and corresponding AIE of the invention. Hydroxymethyl ferrocene was reacted with (3-bromopropyl)trimethoxysilane to obtain the silane precursor, as shown in the following reaction scheme:

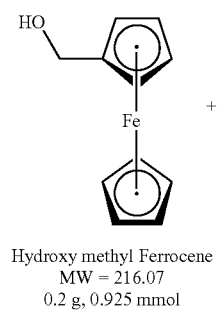

Hydroxy methyl Ferrocene
MW = 216.07
0.2 g, 0.925 mmol

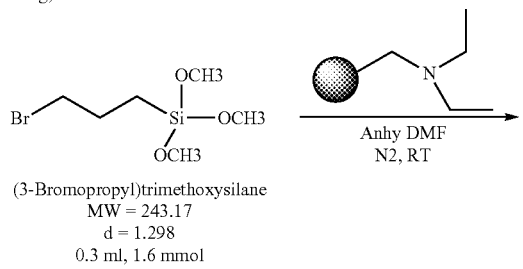

(3-Bromopropyl)trimethoxysilane
MW = 243.17
d = 1.298
0.3 ml, 1.6 mmol

Anhy DMF
N2, RT

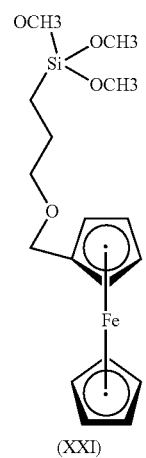

(XXI)
MW = 407.38
Ferrocene tethered solgel precursor/monomer with ether bond

Example 8

Preparation of Ether-Linked Ferrocene Sol-Gel Matrix Material

A preparation of ether-lined ferrocene sol-gel matrix material was prepared, as shown in the following reaction scheme:

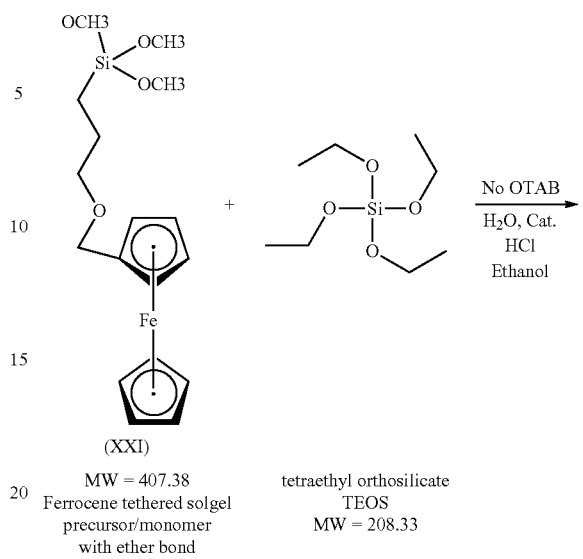

(XXI)
MW = 407.38
Ferrocene tethered solgel precursor/monomer with ether bond tetraethyl orthosilicate
TEOS
MW = 208.33

No OTAB
H2O, Cat.
HCl
Ethanol

Ferrocene tethered solgel via ether bond

Example 9

Preparation of Ether-Linked Ferrocene Sol-Gel Analyte-Insensitive Electrode for Replacement of a Conventional RE The ferrocene (or, more generally, AIM) sol-gel matrix material obtained as described above may be used in the form of a discrete reference electrode, or it may be used in admixture with the ASM sol-gel matrix material described, for example, in Examples 2 or 5. In either case, the AIM and ASM components generate a pH-dependent signal and a pH-independent signal, thus providing a means of internal calibration of the pH response of the sensor.

Example 10

Synthesis of AQ-PVA

Synthesis of AQ-PVA was Prepared, as Shown in the Following Reaction Scheme

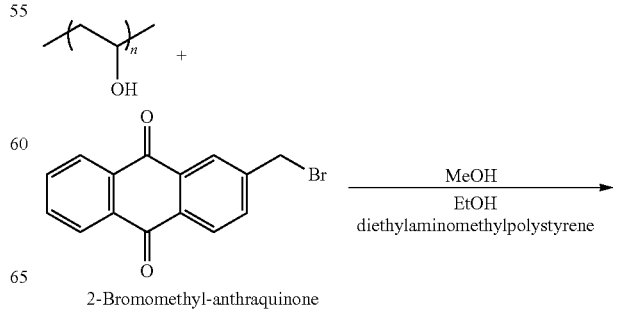

2-Bromomethyl-anthraquinone

MeOH
EtOH
diethylaminomethylpolystyrene

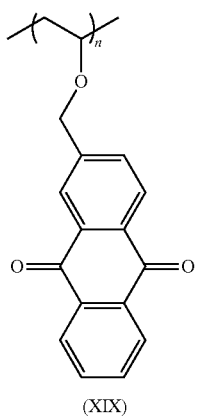

(XIX)

This example and the following example illustrate methods and reagents of the invention for making a non-sol-gel polymer-based matrix and corresponding WE of the invention. Poly(vinyl alcohol) [Alfa Aesar, #41238, CAS 9002-89-5] ((0.29 g, 1 mole) was dissolved in a 1:1 mixture of methanol and ethanol. 2-Bromomethyl anthraquinone (2 g, 6.6 mmole) was added with stirring until completely dissolved. Diethylaminomethylpolystyrene (1 eq.) was added as acid scavenger. The reaction mixture was refluxed for 48 h. The solid formed was removed by filtration, and the liquid fraction was evaporated to dryness.

Example 11

Preparation of AQ-PVA Working Electrode 0.1 g of the PVA-AQ solid product was dissolved in a mixture of 1.5 mL Methanol, 1.5 mL ethanol, and 1.0 mL DMF. The resultant solution was applied as a coating to prepared blank carbon substrate tips, air dried at room temperature, and heat treated at 150° C. for 1 h. Samples of these working electrodes were tested on an Autolab potentiostat with a pH 7 buffer standard at room temperature, with the results shown in Table 3.

TABLE 3

| Sample Code | Peak position (V) | Peak current (μA) |
|---|---|---|
| X070 | −0.486 | 39.4 |
| Y060 | −0.485 | 36.3 |
| X083 | −0.483 | 26.2 |
| Y067 | −0.484 | 32.7 |
| X082 | −0.485 | 29.5 |
| Y077 | −0.485 | 25.2 |

Many of the above Examples illustrate that strong, repeatable signals are obtainable with sensors of the current invention. Their virtually constant peak positions provide the basis for a reliable correlation between potential peak position and the pH value of the standard buffer. It was also seen that different ASM sensing surfaces differ in their electrochemical response, as shown in their peak positions.

What is claimed is:

1. A matrix material comprising a sol-gel or other polymer covalently attached to at least one of an analyte-sensitive material (ASM) and an analyte-insensitive material (AIM), wherein said sol-gel or other polymer is formed by crossing an ASM silane precursor compound having the structure of Formula (IV):

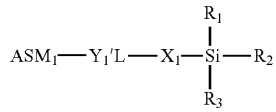

wherein at least two of $R_1$, $R_2$ and $R_3$ are independently alkoxy, aryloxy, or methoxy, and the third is selected from the group consisting of alkyl, aryl, alkoxy, aryloxy, and methoxy; $X_1$ is —O— or a chemical bond; L is a linker; $Y_1'$ is —OCONR$_4$—, —O—, —NR$_4$CO—, —COR$_5$—, —P(O)(OR$_6$)O—, —CO$_2$—, —O$_2$C—, —NO$_2$R$_4$, —CO$_2$NR$_4$—, —N=N—, —CONH—, —NH—, or a chemical bond; ASM$_1$ is an ASM or an AIM; and $R_4$, $R_5$ and $R_6$ are independently hydrogen, alkyl, or aryl.

2. The matrix material of claim 1, wherein $R_1$, $R_2$ and $R_3$ are independently alkoxy; L is —(CH$_2$)$_n$—, $X_1$ is a chemical bond; $Y_1'$ is —CONH—, or —O—, or —NH—; and n is 2-6.

3. The matrix material of claim 1, wherein ASM$_1$ is selected from the group consisting of:

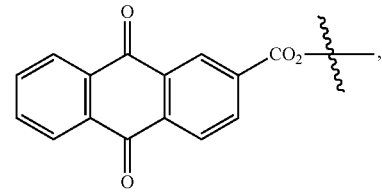

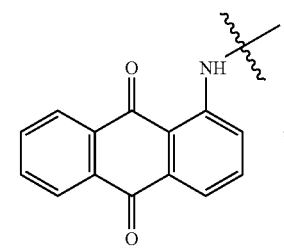

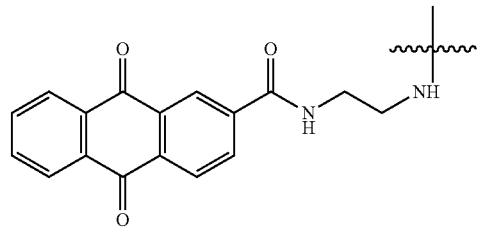

or

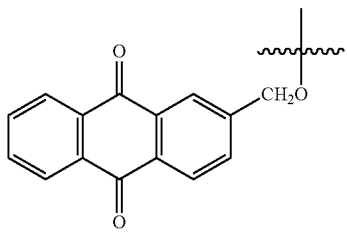

4. The matrix material of claim 1, wherein ASM$_1$ is selected from the group consisting of:

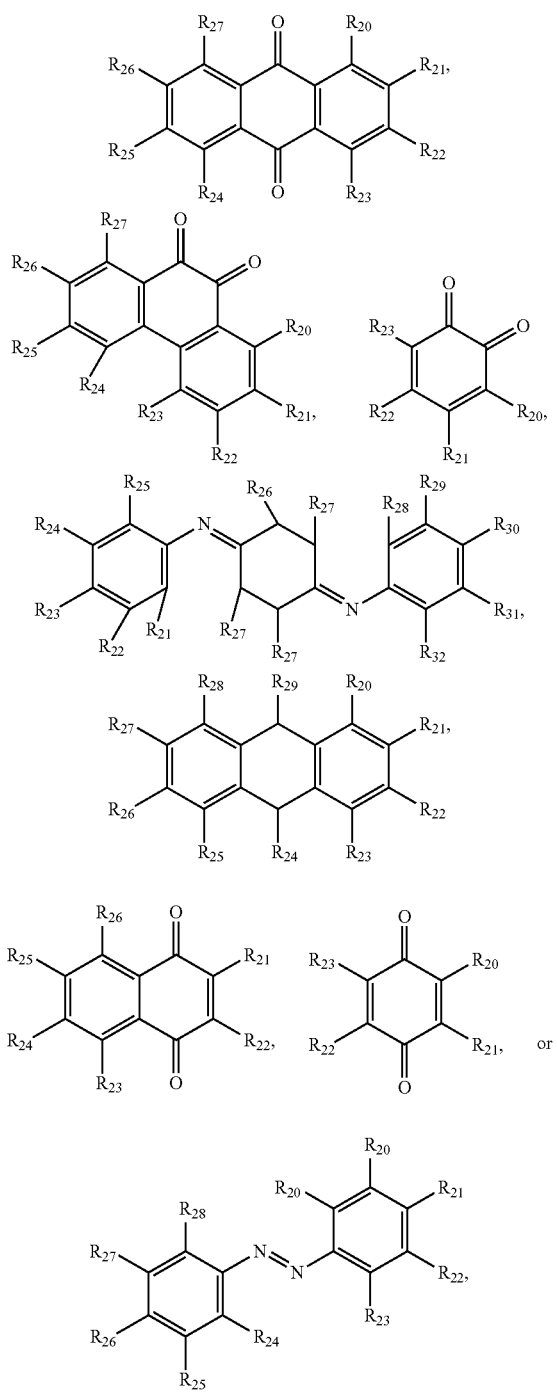

wherein $R_{20}$, $R_{21}$, $R_{22}$, $R_{23}$, $R_{20}$, $R_{24}$, $R_{26}$, $R_{27}$, $R_{28}$, $R_{29}$, $R_{30}$, $R_{31}$, $R_{32}$ and $R_{33}$ are independently hydrogen, —$CO_2H$, halogen, —OH, —$NHR_4$, —$SO_2H$, —$R_5CO$, —P(O)($OR_6$)(OH), —$N_3$, —CN, alkyl, aryl or alkoxy with the proviso that least one substituent is —$CO_2H$, halogen, —OH, —$NHR_4$, —$SO_2H$, —$R_5CO$, —P(O)($OR_6$)(OH), —$N_3$ or —CN.

5. The matrix material of claim 1, wherein said ASM silane precursor compounds of Formula (IV) are selected from the group consisting of:

[structures showing anthraquinone derivatives with Si(OMe)₃ groups via CO-O, CON, and O linkages]

and wherein at least one of said ASM silane precursor compounds are polymerized to form a sol-gel or other polymer of Formula XIX is;

[polymer structure]

(XIX)—(this serves to label that structure as Formula XIX), wherein n is one or more.

6. The matrix material of claim 1, wherein said polymer is selected from the group consisting of polyols, poly(vinyl alcohol), polysulfones, polyethersulfones, polyamides, polyimides, polyesters, vinyl polymers, polyphenylene sulfides, polysaccharides, cellulose, and derivatives, copolymers, blends, and composites of any of the foregoing or combinations of any of the foregoing.

7. An electrode comprising a matrix material of claim 1.

8. The electrode of claim 7, wherein $R_1$, $R_2$ and $R_3$ are either all methoxy or all ethoxy.

9. A pH meter or other analyte sensing device that comprises an electrode of claim 7.

10. A method for preparing the matrix material of claim 1, said method comprising reacting a compound having the general structure of Formula (I):

$$Y_1-L-X_1-\underset{\underset{R_3}{|}}{\overset{\overset{R_1}{|}}{Si}}-R_2 \qquad (I)$$

wherein: at least two and typically all three $R_1$, $R_2$ and $R_3$ are independently alkoxy or aryloxy, and if only two are alkoxy or aryloxy the third may be alkyl or aryl; $X_1$ is —O— or a chemical bond; L is a linker; $Y_1$ is —$CO_2H$, halogen, —OH, —$NHR_4$, —$SO_2H$, —$R_5CO$, —P(O)($OR_6$)(OH), —$N_3$ or —CN; $R_4$, $R_5$ and $R_6$ are independently hydrogen, alkyl or aryl; to form a compound of Formula (IV); and crosslinking said compound of Formula (IV) to form said matrix material.

11. An electrode for use in an analyte sensing device, said electrode comprising a carbon-based substrate material selected from the group consisting of carbon, pyrolytic graphite, graphite, amorphous carbon, carbon black, single- or multi-walled carbon nanotubes, graphene, glassy carbon, boron-doped diamond, pyrolyzed photoresist films, and derivatives thereof, said substrate being non-covalently coated with a cross-linked polymer, wherein said polymer is covalently attached to a redox active material which is an analyte sensitive material (ASM) or an analyte insensitive material (AIM), and said cross-linked polymer material is selected from the group consisting of a sol-gel, a polyol, a poly(vinyl alcohol), a polysulfone, a polyethersulfone, a polyamide, a polysulfonamide, a polyimide, a polyester, and a copolymer of any of the foregoing or combination thereof, wherein said sol-gel or other polymer is formed by crosslinking a compound having the structure of Formula (IV):

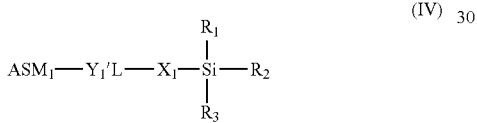
(IV)

wherein at least two of $R_1$, $R_2$ and $R_3$ are independently alkoxy, aryloxy, or methoxy, and the third is selected from the group consisting of alkyl, aryl, alkoxy, aryloxy, and methoxy; $X_1$ is —O— or a chemical bond; L is a linker; $Y_1'$ is —$OCONR_4$, —O—, —$NR_4CO$—, —$COR_5$—, —P(O)($OR_6$)O—, —$CO_2$—, —$O_2C$—, $NO_2R_4$—, —$CO_2NR_4$—, —N=N—, —CONH—, —NH—, or a chemical bond; $ASM_1$ is an ASM or an AIM; and $R_4$, $R_5$ and $R_6$ are independently hydrogen, alkyl, or aryl.

12. The electrode of claim 11, wherein $ASM_1$ is selected from the group consisting of:

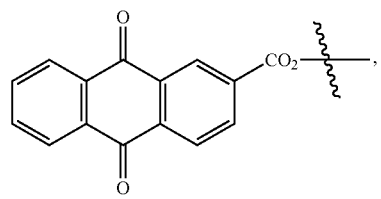

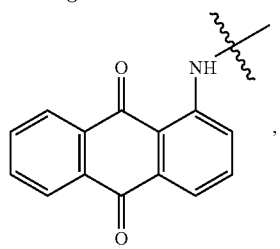

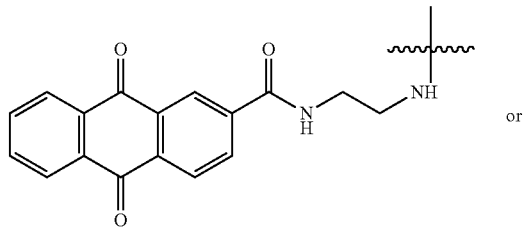 or

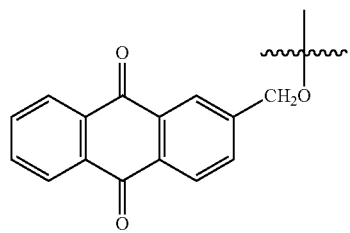

13. The electrode of claim 11, wherein said polymer is poly(vinyl alcohol).

14. The electrode of claim 13, wherein said ASM or AIM is selected from the group consisting of:

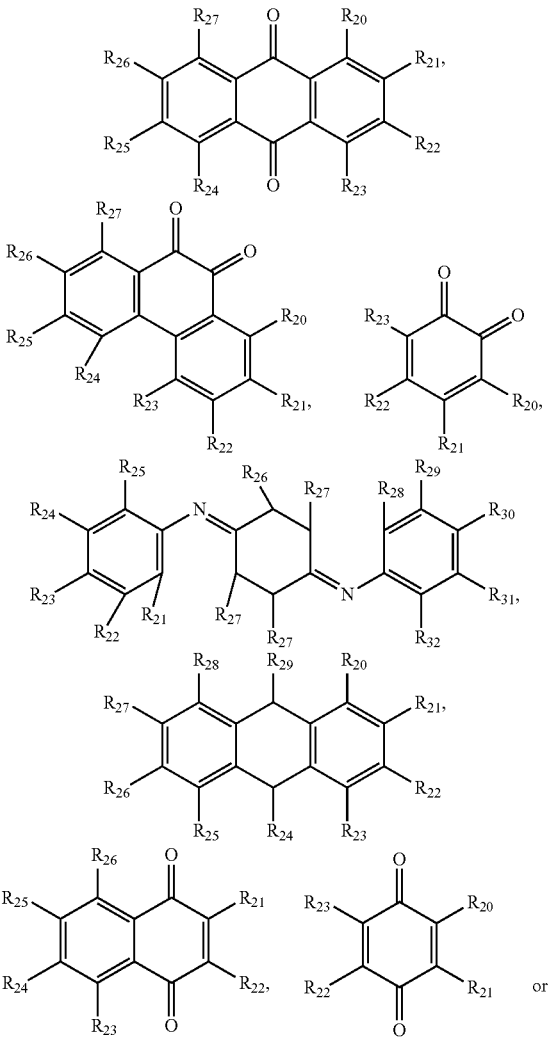

-continued

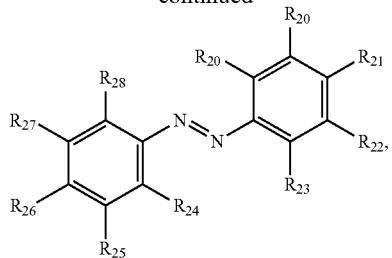

wherein $R_{20}$, $R_{21}$, $R_{22}$, $R_{23}$, $R_{20}$, $R_{24}$, $R_{26}$, $R_{27}$, $R_{28}$, $R_{29}$, $R_{30}$, $R_{31}$, $R_{32}$ and $R_{33}$ are independently hydrogen, —$CO_2H$, halogen, —OH, —$NHR_4$, —$SO_2H$, —$R_5CO$, —$P(O)(OR_6)(OH)$, —$N_3$, —CN, alkyl, aryl or alkoxy with the proviso that least one substituent is —$CO_2H$, halogen, —OH, —$NHR_4$, —$SO_2H$, —$R_5CO$, —$P(O)(OR_6)(OH)$, $N_3$ or —CN.

15. The electrode of claim 11, wherein said polymer is a cross-linked poly(vinyl alcohol) polymer, and said polymer is covalently attached to a redox active material comprising anthraquinone.

* * * * *